United States Patent [19]

Walsh et al.

[11] Patent Number: 4,882,330

[45] Date of Patent: Nov. 21, 1989

[54] 1-ARYLOXY-4-[((4-ARYL)-1-PIPERAZINYL]-2-BUTANOLS USEFUL AS ANTIALLERGY AGENTS

[75] Inventors: David A. Walsh, Richmond; John M. Yanni, Chesterfield, both of Va.

[73] Assignee: A. H. Robins Company, Incorporated, Richmond, Va.

[21] Appl. No.: 333,673

[22] Filed: Apr. 6, 1989

Related U.S. Application Data

[63] Continuation of Ser. No. 933,180, Nov. 21, 1986, abandoned.

[51] Int. Cl.$^4$ ............................................. A61K 31/495
[52] U.S. Cl. ..................................... 514/255; 544/360; 544/398
[58] Field of Search ................. 514/255; 544/360, 398

[56] References Cited

U.S. PATENT DOCUMENTS

| | | | |
|---|---|---|---|
| 3,705,244 | 12/1972 | Manvernay et al. | 514/255 |
| 3,992,536 | 11/1976 | Kleeman et al. | 514/255 |
| 3,997,666 | 12/1976 | Witte et al. | 514/255 |
| 4,203,986 | 5/1980 | Joullie et al. | 514/255 |
| 4,307,097 | 12/1981 | Kanno et al. | 514/255 |
| 4,357,332 | 11/1982 | Kraska et al. | 514/255 |
| 4,379,167 | 4/1983 | Lunsford et al. | 514/652 |
| 4,413,066 | 11/1983 | Kanno et al. | 514/255 |
| 4,451,474 | 5/1984 | Berger et al. | 514/356 |
| 4,463,190 | 7/1984 | Lunsford et al. | 564/349 |
| 4,538,001 | 8/1985 | Lunsford et al. | 568/633 |
| 4,543,362 | 9/1985 | Berger et al. | 514/480 |
| 4,571,394 | 2/1986 | Hays et al. | 514/237 |
| 4,721,715 | 1/1988 | Creuzet et al. | 514/255 |

*Primary Examiner*—Edward A. Miller

[57] ABSTRACT

1-Aryloxy-4-[(4-aryl)-1-piperazinyl]-2-butanols of the formula:

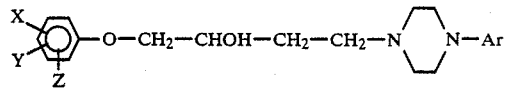

wherein Ar is selected from

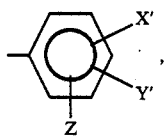

or 2, 3 or 4-pyridyl); X and X' are selected from the group of hydrogen, loweralkyl, loweralkoxy, halogen, trifluoromethyl, nitro, acetylamino, phenyl or

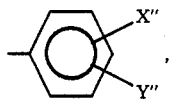

acetyl, cyano, aminocarbonyl, carboxy, or loweralkyl carboxylic acid ester; Y, Y', Y'' are selected from the same group as X and X' except phenyl and substituted phenyl are excluded; Z and Z' are selected from hydrogen, loweralkyl or loweralkoxy and the pharmaceutically acceptable salt thereof are employed in a method of inhibiting or combatting allergic response associated with anaphylactic sensitivity in animals and humans.

51 Claims, No Drawings

1-ARYLOXY-4-[((4-ARYL)-1-PIPERAZINYL]-2-BUTANOLS USEFUL AS ANTIALLERGY AGENTS

This is a continuation, of application Ser. No. 06/933,180, filed Nov. 21, 1986, now abandoned.

BACKGROUND OF THE INVENTION

1. Field of Invention.

This invention relates to a method of combating allergic response in a living animal body in need thereof with 1-aryloxy-4-[(4-aryl)-1-piperazinyl]-2-butanol compounds, more particularly the method of the invention employs the compounds in inhibiting or combating Type I allergic response (Gell & Coombs Classification of Immune Responses). The compounds prevent release of histamine as well as antagonize end organ effects of mediators involved in the immediate hypertensivity response and, as such, are useful in treating allergic phenomena which includes asthma, rhinitis, atopic dermatitis, chronic hives, allergic conjunctivitis, and the like.

2. Information Disclosure Statement.

1-Aryloxy-4-amino-2-butanol compounds having the formula:

wherein, among other radicals, Ar may be phenyl and among other amines, —NR$^1$R$^2$ may be 4-phenyl or 4-pyridylpiperazine, are disclosed in U.S. Pat. Nos. 4,379,167, 4,463,190; and 4,538,001. A continuation-in-part application U.S. Ser. No. 06/904,113 filed Sept. 4, 1986, stemming from the parent application of the foregoing patents and a chain of continuing applications also discloses the bulk of the 1-aryloxy-4-[(4-aryl)-1-piperazinyl]-2-butanols disclosed herein. In the foregoing patents and application the utilities disclosed were betaadrenergic blocking, antihypertensive, antiarrhythmic and local anesthetic. The antiallergenic utility, the basis for the present invention, has not heretofore been disclosed.

1-[3-naphth-1-yloxy)-2-hydroxypropyl]piperazine compounds having the piperazine radical substituted in the 4-position by methoxyphenyl radicals are disclosed in U.S. Pat. No. 3,997,666 as having anti-hypertensive properties and as inhibiting anaphylactoid reactions initiated by dextran in rats.

SUMMARY OF THE INVENTION

The 1-aryloxy-4-[(4-aryl)-1-piperazinyl]-2-butanols useful in the method of this invention have the formula:

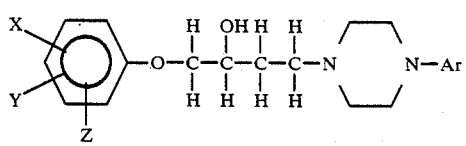

Formula I wherein Ar is selected from

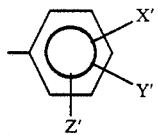

or 2, 3 or 4-pyridyl;

X and X' are selected from the group:
- hydrogen,
- loweralkyl,
- loweralkoxy,
- halogen,
- trifluoromethyl,
- nitro,
- amino,
- acetylamino,
- phenyl, or

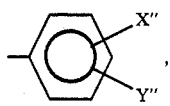

- acetyl,
- cyano,
- aminocarbonyl,
- carboxy,
- or loweralkyl carboxylic acid ester;

Y, Y', Y" and X" are selected from the same group as X and X' except phenyl and substituted phenyl are excluded;

Z and Z' are selected from:
- hydrogen,
- loweralkyl, or
- loweralkoxy;

and the pharmaceutically acceptable salts thereof.

In the further definition of symbols in the formulas hereof and where they appear throughout this specification and in the claims, the terms have the following significance.

The term "loweralkyl" as used herein unless otherwise specified, includes straight and branched chain radicals of up to eight carbons inclusive and is exemplified by such groups as methyl, ethyl, propyl, isopropyl, butyl, sec. butyl, tert-butyl, amyl, isoamyl, hexyl, heptyl, and octyl radicals and the like. The term "loweralkoxy" has the formula -O-loweralkyl.

The term "halo" or "halogen" when referred to herein includes fluorine, chlorine, bromine, and iodine unless otherwise stated.

"Pharmaceutically acceptable salts" include acid addition salts, alcoholates, quaternary salts and carboxylic acid salts and hydrates of the free bases and salts when they occur which are physiologically compatible in warm blooded animals. The acid addition salts may be formed by either strong or weak acids. Representative of strong acids are hydrochloric, hydrobromic, sulfuric and phosphoric acids. Representative of weak acids are fumaric, maleic, mandelic, tartaric, citric, oxalic, succinic, hexamic, and the like. Suitable quaternary salts include loweralkyl halides and loweralkyl sulfates. Suitable carboxylic acid salts are formed by such as the alkali metals, alkaline earth metals, copper, aluminum, and the like. Suitable quaternary salts include the loweralkyl halides and loweralkyl sulfates.

Salts of compounds of Formula I may be converted to the free base by partitioning between a solvent such as methylene chloride and an aqueous base such as sodium hydroxide and evaporating the solvent layer in vacuo.

The primary screening method used to detect antiallergy properties of the compounds of Formula I is the passive anaphylaxis (PFA) screen test, a modification of the procedure of R. R. Martel and J. Klicius, Intern. Arch. Allergy. Appl. Immunology, Vol. 54, pp 205–209 (1977) which measures the effect of oral administration of the compound on the volume of a rat paw which was previously injected with anti-egg albumin serum and is described in detail under Pharmacology Methods hereinbelow.

A method of studying potency in preventing guinea pig anaphylaxis relative to known anti-allergy drugs is also described hereinbelow.

The Gell and Coombs Classification of Immune Responses referred to hereinabove is well known in the art and is described in ESSENTIAL IMMUNOLOGY, 3rd Ed. (1977), (Blackwell Scientific Publications) printed by William Clowes & Sons, Limited, London, Beccles & Colchester.

The method used for preparing the 1-aryloxy-4-chloro-2-butanols intermediates used in the preparation of compounds of Formula I is generally that disclosed in U.S. Pat. No. 4,463,190 and is diagrammed in Chart I wherein all the symbols have the meaning given under Formula I above.

CHART I

Preparation of Starting 1-Phenoxy-4-chloro-2-butanols

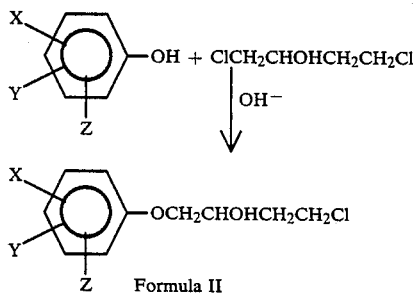

Formula II

The 1-aryloxy-4-chloro butanols (I) are generally prepared by treating an aqueous basic solution or an aqueous alcoholic basic solution of a phenol, a substituted phenol with 1,4-dichloro-2-butanol. The addition is carried out at or below 70° C., preferably at about 30° C. to 65° C. over a period of from about 3 hr to about 8 hr. Subsequent to the addition, the reaction mixture is heated from about 50° C. to about 75° C., preferably at 60°–70° C. for a period of time of from about six hours to about 48 hours, usually for a period of from twelve hours to eighteen hours. The 1-aryloxy-4-chloro-2-butanol is isolated from the reaction mixture by extraction using a suitable organic solvent as, for example, ether, isopropyl ether, or chloroform, evaporation of the solvent after drying to give the 1-aryloxy-4-chloro-2-butanol which is isolated by suitable means such as distillation or crystallization. Alternatively, the 1-aryloxy-4-chloro-2-butanol can be prepared by adding an aqueous basic solution to a mixture of the phenol and 1,4-dichloro-2-butanol at a rate so as to maintain the reaction mixture at a pH of from about 9.0 to about 10.5, preferably at a pH of 9.5 to 10.0. The product is isolated as described above.

The starting arylpiperazines were purchased or prepared by standard procedures (see Join, P.C. et al. in J. MED. CHEM. 10, 1967, p. 812) and are generally known compounds.

The following preparations are given by way of illustration only and are in no way to be construed as limiting.

PREPARATION 1

4-Chloro-1-phenoxy-2-butanol

To a mixture which contained 282 g (3 moles) of phenol, one liter of water and 300 ml of 50% sodium hydroxide was added slowly with stirring at 60° C., 443.36 g (3.1 mole) of 1,4-dichlorobutanol. Stirring was continued at 60° C. for 16 hr. The resulting mixture was extracted twice with one liter of ether and the combined ether extracts were washed with water to neutrality and dried overnight over sodium sulfate. The dried ether mixture was concentrated to dryness under reduced pressure. The residue was distilled and yielded 435 g of product which was collected at 135°–138° C./0.05 mm. The product solidified and was recrystallized using petroleum ether (60°–110° C.) to give a white crystalline solid which melted at 52°–54° C.

Analysis: Calculated for $C_{10}H_{13}ClO_2$: C, 59.86; H, 6.53;

Found: C, 59.72; H, 6.37.

PREPARATION 2

4-Chloro-1-(2-chlorophenoxy)-2-butanol

To a mixture of 129 g (1 mole) of 2-chlorophenol, 60 g of potassium hydroxide, 100 ml of water and 400 ml of isopropanol was added 1.3 mole (185.9 g) of 1,4-dichloro-2-butanol with stirring at 50° C. The resulting mixture was heated in a steam bath at 65° C. overnight and extracted with 300 ml of isopropyl ether. The ether extract was washed successively with 1N sodium hydroxide, water and dried over sodium sulfate. The dried ether solution was concentrated and the oily residue was distilled under reduced pressure yielding 152 g of an oily substance (b.p. 130°–131° C./0.01 mm).

Analysis: Calculated for $C_{10}H_{15}ClO_2$: C, 51.08; H, 5.15;

Found: C, 51.13; H, 5.14.

PREPARATION 3

4-Chloro-1-(3,5-dimethylphenoxy)-2-butanol

To a mixture of 245 g (2 mole) of 3,5-dimethylphenol and 2 liters of 2N sodium hydroxide was added 2.5 moles of 1,4-dichlorobutanol with stirring at 65° C. overnight. The solid precipitate which separated on cooling was filtered and washed with water to neutrality. Recrystallization with isopropyl ether yielded 375 g of white crystalline solid which melted at 74°–76° C.

Analysis: Calculated for $C_{12}H_{17}ClO_2$: C, 62.02; H, 7.49;

Found: C, 63.96; H, 7.66.

PREPARATION 4

4-Chloro-1-(4-chloro-3-methylphenoxy)-2-butanol

To a mixture of 286 g (2 mole) of 3-methyl-4-chlorophenol, 700 ml of tertiary butanol, 700 ml of water and 3.0 mole of 1,4-dichloro-2-butanol, sodium hydroxide (2.9 moles, 230 g in 700 ml of water) was added with stirring at 40° C. to maintain a pH of 9.5-10.0 as the reaction progressed. The addition was 10 hr; the reaction was stirred at 40° C. for 48 hr. The resulting reaction mixture was extracted with chloroform sodium hydroxide at 25° C. The chloroform extract was washed with sodium sulfate. The dried chloroform solution was concentrated and the residue was distilled under reduced pressure to give 110.9 g of the product which distilled at 135°-143° C./0.007 mm and melted at 87°-89° C. after recrystallization with isopropanol and petroleum ether (30°-60° C.).

Analysis: Calculated for $C_{11}H_{14}Cl_2O_2$: C, 53.03; H, 5.66;

Found: C, 53.11; H, 5.61.

PREPARATION 5

4-Chloro-1-(4-chloro-2-methylphenoxy)-2-butanol

4-Chloro-1(4-chloro-2-methylphenoxy)-2-butanol was prepared according to the procedure of Preparation 4 using 105 g (0.74 mole) of 2-methyl-4-chlorophenol, 171.5 g (1.2 mole) of 1,4-dichloro-2-butanol, 50.3 g of sodium hydroxide, 300 ml of water and 300 ml of tertiary butanol. There was obtained 84 g (45.5%) of product which distilled at 135° C./0.01 mm.

Analysis: Calculated for $C_{11}H_{14}O_2Cl_2$: C, 53.03; H, 5.66;

Found: C, 53.41; H, 5.70.

PREPARATION 6

4-Chloro-(4-biphenylyloxy)-2-butanol

To a solution of 1 mole (158 g) of 4-phenylphenol, 100 g of sodium hydroxide and 400 ml of water was added 1 mole (143.02 g) of 1,4-dichloro-2-butanol with stirring at 40° C. The resulting mixture was heated at 68° C. in a steam bath for 6 hr, cooled and extracted with 300 ml of chloroform. The chloroform extract was washed with water to neutrality, dried over sodium sulfate and concentrated to dryness. The solid residue was recrystallized with isopropanol and yielded 180 g of a white crystalline solid which melted at 123°-124° C.

Analysis: Calculated for $C_{16}H_{17}ClO_2$: C, 69.44; H, 6.19;

Found: C, 69.79; H, 6.22.

PREPARATION 7

4-Chloro-1-(3-trifluoromethylphenoxy)-2-butanol

To a mixture of 0.5 mole (75 g) of m-trifluoromethylphenol, 1 mole (56 g) of potassium hydroxide, 100 ml of water and 400 ml of isopropanol was added 0.6 mole (84 g) of 1,4-dichloro-2-butanol with stirring at temperature below 55° C. The resulting reaction mixture was heated at 65° C. for 20 hr, mixed with 2 liters of water, and extracted with 400 ml of isopropyl ether. The ether extract was washed with 0.5 N sodium hydroxide and then with water, dried over sodium sulfate and distilled under reduced pressure. The distillate which was collected at 120°-124° C./0.01 mm solidified at room temperature and melted at 50°-52° C.

Analysis: Calculated for $C_{11}H_{12}ClF_3O_2$: C, 49.18; H, 4.50;

Found: C, 49.35; H, 4.47.

PREPARATION 8

4-Chloro-1-(4-chlorophenoxy)-2-butanol

4-Chloro-1-(4-chlorophenoxy)-2-butanol was prepared using the procedure of Preparation 7 from 45 g (0.5 mole) pf p-chlorophenol, 72 g (0.5 mole) of 1,4-dichloro-2-butanol, 40 g (1.0 mole) of sodium hydroxide and 400 ml of water to give 85 g (36.1%) of product which melted at 62°-64° C. after recrystallization from isopropanol.

Analysis: Calculated for $C_{10}H_{15}ClO_2$: C, 51.09; H, 5.14;

Found: C, 51.76; H, 5.12.

PREPARATION 9

4-Chloro-1-(2-methoxyphenoxy)-2-butanol

To a mixture of 2 moles (248.26 g) of 2-methoxyphenol, 4 moles (160 g) of sodium hydroxide, 250 ml of water and 1 liter of isopropanol was added with stirring 2.2 moles (314.64 g) of 1,4-dichloro-2-butanol. The mixture was refluxed gently overnight. The reaction mixture was extracted with 1 liter of isopropyl ether, dried over sodium sulfate and distilled under reduced pressure. The distillate which was collected at 136°-138° C./0.015 mm (395.8 g) solidified to a white crystalline solid which melted at 48°-50° C.

Analysis: Calculated for $C_{11}H_{14}O_3Cl$: C, 57.52; H, 6.14;

Found: C, 57.49; H, 6.54.

Using the procedures disclosed in Preparations 1-9, starting from the appropriate phenol and 1,4-dichloro-2-butanol, various other 1-phenoxy-4-chloro-2-butanols are prepared in Preparations 10 to 15.

PREPARATION 10

4-Chloro-1-(2-methyl-5-chlorophenoxy)-2-butanol, b.p. 135°-8° C./0.05 mm was prepared from 2-methyl-5-chlorophenol and 1,4-dichloro-2-butanol.

PREPARATION 11

4-Chloro-1-(4-acetylaminophenoxy)-2-butanol, m.p. 125°-128° C., was prepared from 4-acetylaminophenol and 1,4-dichloro-2-butanol.

PREPARATION 12

4-Chloro-1-(3-chlorophenoxy)-2-butanol, 60°-62° C., was prepared from 3-chlorophenol and 1,4-dichloro-2-butanol.

PREPARATION 13

4-Chloro-1-(2-ethoxyphenoxy)-2-butanol, b.p. 130°-132° C./0.01 mm was prepared from 2-ethoxyphenol and 1,4-dichloro-2-butanol.

PREPARATION 14

4-Chloro-1-(4-acetylphenoxy)-2-butanol, m.p. 125°-128° C. was prepared from 4-acetylphenol and 1,4-dichloro-2-butanol.

PREPARATION 15

4-Chloro-1-(o-phenylphenoxy)-2-butanol, b.p. 156°-160° C./0.25 mm. was prepared from o-phenylphenol and 1,4-dichloro-2-butanol.

PREPARATION 16

1-(4-Bromophenoxy)-4-chloro-2-butanol

To a rapidly stirring solution of 22.5 g (0.56 mole) of sodium hydroxide in 400 ml of water was added, dropwise, 73.8 g (0.52 mole) of freshly distilled 1,4-dichloro-2-butanol. The mixture was stirred for 15 min at ambient temperature. To this mixture was added, over a 45 min period, a solution obtained by adding 75.0 g (0.43 mole) of 4-bromophenol to a solution of 18.0 g (0.47 mole) of sodium hydroxide in 430 ml of water. The mixture was stirred vigorously for 30 hr and then cooled in an ice bath. The suspended solid was collected by filtration, rinsed with water several times and air dried. Recrystallization from ethyl ether-petroleum ether (b.p. range 30°-60° C.) gave 44.2 g (37%) of white solid, m.p. 75°-78° C.

Analysis: Calculated for $C_{10}H_{12}BrClO_2$: C, 42.96; H, 4.33;
Found: C, 43.16; H, 4.34.

PREPARATION 17

4-Chloro-1-(4-fluorophenoxy)-2-butanol

Utilizing the procedure of Preparation 16, 1,4-dichloro-2-butanol was reacted with 4-fluorophenyl to give white title compound, m.p. 53°-55° C. in 30% yield.

Analysis: Calculated for $C_{10}H_{12}ClFO_2$: C, 54.93; H, 5.53;
Found: C, 55.20; H, 5.56.

PREPARATION 18

4-Chloro-1-(4-methylphenoxy)-2-butanol

Utilizing the procedure of Preparation 16, 1,4-dichloro-2-butanol was reacted with 4-methylphenol to give white title compound, m.p. 62°-64° C. in 42% yield.

Analysis: Calculated for $C_{11}H_{15}ClO_2$: C, 61.54; H, 7.04;
Found: C, 61.62; H, 7.17.

PREPARATION 19

4-Chloro-1-(4-methoxyphenoxy)-2-butanol

Utilizing the procedure of Preparation 16, 1,4-dichloro-2-butanol was reacted with 4-methoxyphenol to give white title compound, m.p. 65°-68° C. in 42% yield. The recrystallizing solvent was diethyl ether.

Analysis: Calculated for $C_{11}H_{15}ClO_3$: C, 57.27; H, 6.55;
Found: C, 57.39; H, 6.62.

PREPARATION 20

4-Chloro-1-(4-nitrophenoxy)-2-butanol

Utilizing the procedure of Preparation 16, 1,4-dichloro-2-butanol was reacted with 4-nitrophenol to give white title compound, m.p. 60°-63° C.

Analysis: Calculated for $C_{10}H_{12}ClNO_4$: C, 48.89; H, 4.92; N, 5.71;
Found: C, 48.92; H, 4.94; N, 5.86.

PREPARATION 21

4-Chloro-1-(3,4-dichlorophenoxy)-2-butanol

Utilizing the procedure of Preparation 16, 1,4-dichloro-2-butanol was reacted with 1,4-dichloro-2-butanol to give white title compound, m.p. 82°-84° C. in 35% yield.

Analysis: Calculated for $C_{10}H_{11}Cl_3O_2$: C, 44.56; H, 4.11;
Found: C, 44.76; H, 4.17.

PREPARATION 22

4-(4-Chloro-2-hydroxybutoxy)benzonitrile

Utilizing the procedure of Preparation 16, 1,4-dichloro-2-butanol was reacted with 4-cyanophenol to give white title compound, m.p. 78°-80° C. in 13% yield.

Analysis: Calculated for $C_{11}H_{12}ClNO_2$: C, 58.55; H, 5.36; N, 6.21;
Found: C, 58.61; H, 5.41; N, 6.23.

PREPARATION 23

4-Chloro-1-[4-(1,1-dimethylethyl)phenoxy]-2-butanol

Utilizing the procedure of Preparation 16, 1,4-dichloro-2-butanol was reacted with 4-t-butylphenol to give white title compound, m.p. 45°-47° C. Petroleum ether (30°-60° C.) was the recrystallizing solvent.

Analysis: Calculated for $C_{14}H_{21}ClO_2$: C, 65.49; H, 8.24;
Found: C, 65.57; H, 8.31.

PREPARATION 24

4-(4-Chloro-2-hydroxybutoxy)benzamide

Utilizing the procedure of Preparation 16, 1,4-dichloro-2-butanol was reacted with 4-hydroxybenzamide to give white title compound, m.p. 150°-153° C. in 25% yield. The recrystallizing solvent was 95% ethanol.

Analysis: Calculated for $C_{11}H_{14}ClNO_3$: C, 54.22; H, 5.79; N, 5.75;
Found: C, 54.24; H, 5.78; N, 5.71.

PREPARATION 25

1-[4-(4-Chloro-2-hydroxybutoxy)phenyl]ethanone

Utilizing the procedure of Preparation 16, 1,4-dichloro-2-butanol was reacted with 4-hydroxyacetophenone to give cream colored solid, m.p. 75°-77° C. Recrystallizing solvent was a mixture of ethanol-diethyl ether.

Analysis: Calculated for $C_{12}H_{15}ClO_3$: C, 59.39; H, 6.23;
Found: C, 59.57; H, 6.34.

PREPARATION 26

N-[4-(4-Chloro-2-hydroxybutoxy)phenyl]acetamide

To a solution of 500 g (3.5 mole) of 1,4-dichloro-2-butanol was added, dropwise, 500 ml (6.25 mole) of a 50% sodium hydroxide solution. The mixture was stirred for 16 hr and then 500 ml of water was added, dropwise, with the temperature maintained below 35° C. The mixture was extracted with 500 ml of isopropyl ether, dried over sodium sulfate and concentrated to give an oil which was purified by distillation. To 14.3 g (0.1 mole) of the purified epoxide was added a solution of 15.1 g (0.1 mole) of 4-acetamidophenol in 150 ml of 2-propanol and 4 g of (0.1 mole) of sodium hydroxide in 10.0 ml of water. The mixture was stirred for 15 hr and then poured into 400 ml of water at 0° C. The crude, collected solid was washed with water and allowed to air dry. The solid was suspended in 350 ml of acetone, collected by filtration, and washed with additional portions of acetone. The filtrate was concentrated under reduced pressure to give 13.8 g (53% yield) of solid. A portion of this solid was recrystallized from tetrahydrofuran to give cream-colored solid, m.p. 124°–127° C.

Analysis: Calculated for $C_{12}H_{16}ClNO_3$: C, 55.93; H, 6.26;
N, 5.44;
Found: C, 56.19; H, 6.38;
N, 5.44.

PREPARATION 27

1-(3,4,5-Trimethoxyphenyl)piperazine

A solution of 44.3 g (0.25 mole) of bis(2-chloroethyl)amine hydrochloride and 45.5 g (0.25 mole) of 3,4,5-trimethoxyaniline in 550 ml of absolute ethanol was heated at reflux for 16 hr under a nitrogen atmosphere. The mixture was cooled and 50.0 g (0.36 mole) of potassium carbonate was added and heating was continued for 16 hr. The hot mixture was filtered, the filtrate was concentrated under reduced pressure and the residue was triturated with ethyl acetate to obtain the crude hydrochloride. The collected solid was recrystallized from 2-propanol/methanol and dissolved in 5.9 sodium hydroxide. The solution was continuously extracted with chloroform for 5 hr. The organic layer was dried over magnesium sulfate, concentrated under reduced pressure and the residue was triturated with cyclohexane/petroleum ether (30°–60° C.) to give 23.6 g (38%) of white solid, m.p. 73°–77° C.

Analysis: Calculated for $C_{13}H_{10}N_2O_3$: C, 61.89; H, 7.99;
N, 11.10;
Found: C, 61.53; H, 8.01;
N, 11.01.

PREPARATION 28

1-(3,4-Dichlorophenyl)piperazine

This compound was prepared according to the procedure of Preparation 1. A mixture of 44.6 g (0.25 mole) of bis(2-chloroethyl)amine hydrochloride, 40.5 g (0.25 mole) of 3,4-dichloroaniline and 50.0 g (0.36 mole) of potassium carbonate in a total volume of 500 ml of n-butanol gave an oil as residue. Trituration of the oil with petroleum ether (30°–60° C.) gave 16.0 g (28%) of white solid, m.p. 62°–65° C.

Analysis: Calculated for $C_{10}H_{12}Cl_2N_2$: C, 51.97, H, 5.23;
N, 12.12;
Found: C, 51.75; H, 5.24;
N, 12.01.

PREPARATION 29

1-(4-Bromophenyl)piperazine monohydrochloride

This compound was prepared according to the procedure of Preparation 1. A mixture of 5.4 g (0.03 mole) of bis(2-chloroethyl)amine hydrochloride, 5.2 g (0.03 mole) of p-bromoaniline and 5.0 g (0.04 mole) of solid potassium carbonate in a total volume of 50 ml of absolute ethanol gave 2.9 g (26%) of a semisolid. A 0.5 g portion of the base was converted to the hydrochloride using ethereal hydrogen chloride which was recrystallized from methanol/ethyl ether to give white solid, m.p. 240° C. with decomposition.

Analysis: Calculated for $C_{10}H_{14}BrClN_2$: C, 43.27; H, 5.11;
N, 10.12;
Found: C, 43.10; H, 5.08;
N, 10.09.

PREPARATION 30

4-(1-Piperazinyl)benzonitrile monohydrochloride

A mixture of 27.3 g (0.15 mole) of p-bromobenzonitrile, 38.7 g (0.45 mole) of piperazine and 42.0 g (0.30 mole) of solid potassium carbonate in a total volume of 60 ml of n-butanol was heated at reflux for 16 hr under a nitrogen atmosphere. The mixture was concentrated under reduced pressure and the slurry partitioned between 10% sodium hydroxide and chloroform. The chloroform layer was separated, dried over magnesium sulfate and concentrated under reduced pressure to give an oil. The oil was eluted through a 400 g silica gel column with a 10% methanol in methylene chloride mixture. The appropriate fractions were concentrated under reduced pressure to give a golden oil. Trituration of this oil with ethyl acetate gave a white powder. The collected white powder was stirred for 15 min in ethereal hydrogen chloride and recrystallized from methanol-water to give 1.5 g (4.5%)* of white solid, m.p. 160° C. with decomposition.

* A limited product yield was obtained due to the fact that the piperazine starting material was not anhydrous. When anhydrous piperazine was used, the yield of the reaction was 20%.

Analysis: Calculated for $C_{11}H_{14}ClN_3$: C, 59.06; H, 6.31;
N, 18.78;
Found: C, 58.90; H, 6.32;
N, 18.86.

PREPARATION 31

4-(1-Piperazinyl)benzamide

To 8.0 g (0.04 mole) of 4-(1-piperazinyl)benzonitrile was added, with stirring, 50.0 ml (0.87 mole) of 93% sulfuric acid over a 15 min period. The mixture was stirred overnight and the resulting suspended amide was collected by filtration, rinsed with water, and allowed to air dry. The solid was recrystallized from absolute ethanol to give 1.6 g (20%) of white solid, m.p. 240°–243° C.

Analysis: Calculated for $C_{11}H_{15}N_3O$: C, 64.37; H, 7.37; N, 20.47;
Found: C, 64.20; H, 7.33; N, 20.34.

PREPARATION 32

1-(4-Nitrophenyl)-4-(phenylmethyl)piperazine

To 12.5 g (0.07 mole) of mechanically stirred 1-benzylpiperazine was added 10.0 g (0.07 mole) of 4-nitrofluorobenzene. After 10 minutes the mixture solidified. The yellow solid was suspended in 50 ml of ethyl acetate and ethereal hydrogen chloride was slowly added to the stirring mixture under a nitrogen atmosphere. The solid was collected (filtration) and partitioned between 10% sodium hydroxide solution and benzene. The benzene layer was washed with ten 100 ml portions of water, dried with anhydrous magnesium sulfate and concentrated under reduced pressure to give a yellow oil. Upon cooling, the oil crystallized. The solid was recrystallized from 2-propanol/petroleum ether (60°–110° C.) to give 9.8 g (47%) of yellow solid, m.p. 115°–118° C.

Analysis: Calculated for $C_{17}H_{19}N_3O_2$: C, 68.67; H, 6.44;
N, 14.13;
Found: C, 68.87; H, 6.43;
N, 14.18.

PREPARATION 33

4-[4-(Phenylmethyl)-1-piperazinyl]benzeneamine dihydrochloride

This compound was prepared by the hydrogenation of 9.8 g (0.03 mole) of 1-(4-nitrophenyl)-4-(phenylmethyl) piperazine in 200 ml of benzene using palladium on carbon as the catalyst. The solution was filtered and the filtrate concentrated to an oil under reduced pressure. Upon cooling, the oil crystallized to a dark purple mass. The solid was triturated with petroleum ether (60°–110° C.) for 1 hr and 9.5 g (50%) of light purple product was collected by filtration. One gram of this unstable solid was converted to the hydrochloric acid salt using ethereal hydrogen chloride and recrystallized from methanol/ethyl ether to give 100 mg of light purple solid, m.p. >240° C.

Analysis: Calculated for $C_{17}H_{23}Cl_2N_3$: C, 60.00; H, 6.81;
N, 12.35;
Found: C, 60.09; H, 6.83;
N, 12.33.

PREPARATION 34

N-[4-[4-(Phenylmethyl)-1-piperazinyl]phenyl]acetamide

To a solution of 8.5 g (0.03 mole) of the base of 4-[4-(phenylmethyl)-1-piperazinyl]benzeneamine and 16.0 g (0.16 mole) of triethylamine in 450 ml of ethyl acetate was added, dropwise, a solution of 2.5 g (0.035 mole) of acetyl chloride in 50 ml of ethyl acetate. The mixture was magnetically stirred for 3 hr and then heated at reflux for 1 hr. The excess acetyl chloride was co-distilled with benzene and the resulting oil was shaken in 400 ml of 10% sodium hydroxide solution. The suspended tan solid was collected by filtration, washed thrice with 100 ml portions of water, and dir dried to give 9.7 g (99%) of crude product. A one gram portion was recrystallized from benzene/petroleum ether to give 100 mg of cream colored solid, m.p. 159°–161° C.

Analysis: Calculated for $C_{19}H_{23}N_3O$: C, 73.76; H, 7.49; N, 13.58;
Found: C, 73.65; H, 7.44; N, 13.48.

PREPARATION 35

N-[4-(1-Piperazinyl)phenyl]acetamide

This compound was prepared by the hydrogenation of 7.7 g (0.025 mole) of N-[4-[4-(phenylmethyl)-1-piperazinyl]phenyl]acetamide in 100 ml of methanol using palladium on carbon as the catalyst. The solution was filtered and the filtrate concentrated under reduced pressure to give an oil which crystallized. The solid was dissolved in a minimum amount of a methylene chloride/10% methanol solution and passed through a 100 g Florisil ® column. The desired frations were concentrated to an oil under reduced pressure which crystallized to give 3.1 g (56%) of crude product. A 0.5 g portion was recrystallized from methanol/petroleum ether to give cream colored solid, m.p. 191°–193° C.

Analysis: Calculated for $C_{12}H_{17}N_3O$: C, 65.73; H, 7.81;
N, 19.16;
Found: C, 65.64; H, 7.75;
N, 19.10.

PREPARATION 36

4-(1-Piperazinyl)benzoic acid ethyl ester monohydrochloride

To 3.1 g (0.015 mole) of 4-(1-piperazinyl)benzamide suspended in 5.0 ml (0.09 mole) of 95% ethyl alcohol was added, dropwise, 3.0 ml (0.06 mole) of 90% sulfuric acid under ice bath temperature. The mixture was heated at reflux for 5 hr and then neutralized with 10% sodium hydroxide under ice bath temperature. The suspended solid (starting material) was collected by filtration and the filtrate was extracted thrice with 25 ml portions of benzene. The combined benzene extracts were dried (magnesium sulfate) and concentrated under reduced pressure to give a golden oil. The hydrochloride was formed in 2-propanol saturated with hydrogen chloride and the collected solid, 1.1 g, (31%) was recrystallized from 2-propanol to give 0.5 g of white crystalline solid, m.p. 203°–206° C.

Analysis: Calculated for $C_{13}H_{19}ClN_2O_2$: C, 57.67; H, 7.07;
N, 10.35;
Found: C, 57.52; H, 7.13;
N, 10.38.

PREPARATION 37

Following the procedure of Preparation 16 and substituting the following commercially available phenols for 4-bromophenol:
4-chloro-3,5-dimethylphenol,
2-chloro-4,5-dimethylphenol,
4-bromo-2,6-dimethylphenol, and
2,4-dichloro-6-nitrophenol,
there are obtained:
1-(4-chloro-3,5-dimethylphenoxy)-4-chloro-2-butanol,
1-(2-chloro-4,5-dimethylphenoxy)-4-chloro-2-butanol,
1-(4-bromo-2,6-dimethylphenoxy)-4-chloro-2-butanol, and
1-(2,4-dichloro-6-nitrophenoxy)-4-chloro-2-butanol.

The synthesis of the 1-aryloxy-4-[(4-aryl)-1-piperazino]-2-butanol compounds of Formula I useful in the method of this invention is generally that disclosed in U.S. Pat. No. 4,463,190 and sketched in Chart II wherein the symbols have the meaning given under Formula I above.

CHART II

Preparation of
1-aryloxy-4-[(4-aryl)-1-piperazino]2-butanols

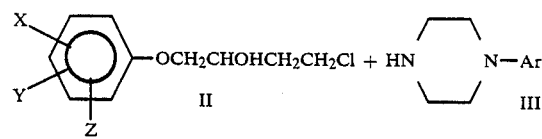

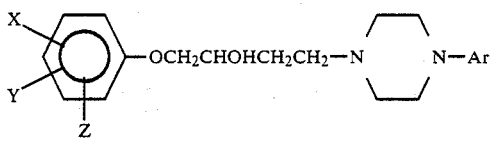

Generally, a mixture of a 4-chloro-1-phenoxy-2-butanol (II) and 1-aryl-piperazine (III) in a suitable solvent, preferably butanol, together with anhydrous sodium carbonate, preferably with a small amount of potassium iodide catalyst, is heated, preferably at reflux temperature of butanol until reaction is complete, usually within 20 hr time. A suitable work-up procedure is to concentrate the reaction mixture, partition the residue between water or aqueous basic solution and a suitable organic solvent, e.g., benzene, wash, dry, and concentrate the organic solvent layer to give an oily residue. The oil will either crystallize to give the free base or a pharmaceutical salt is prepared and crystallized out. In either case the product may be purified by recrystallization from a suitable solvent.

The following examples illustrate the preparation of compounds of Formula I useful in the antiallergy method of this invention and are not intended to be limiting. Structures of compounds prepared in the examples are illustrated in Table I.

EXAMPLE 1

1-(2-Chlorophenoxy)-4-(4-phenyl-1-piperazinyl)-2-butanol

A mixture of 35.1 g (0.15 mole) of 1-(o-chlorophenoxy)-2-hydroxybutyl chloride, 32.6 g (0.2 mole) of N-phenylpiperazine and 400 ml of 2-propanol was heated at reflux for 48 hr. The resulting reaction mixture was allowed to stand in a refrigerator overnight and filtered. The filtrate was treated with ethereal hydrogen chloride and precipitated with ether. Upon filtering, a white crystalline solid formed which was dissolved in dilute hydrochloric acid and the mixture was then neutralized with aqueous sodium hydroxide producing a crystalline precipitate. This was recrystallized with isopropanol yielding 36 g of the free base, m.p. 100°–101.5° C.

Analysis: Calculated for $C_{20}H_{25}N_2O_2Cl$: C, 66.56; H, 6.98;
N, 7.76;
Found: C, 66.49; H, 7.03;
N, 7.86.

EXAMPLE 2

1-(4-CHloro-2-methylphenoxy)-4-(4-phenyl-1-piperazinyl)-2-butanol dihydrochloride A mixture of 18.72 g (0.075 mole) of 1-(4-chloro-2-methylphenoxy)-2-hydroxybutyl chloride, 16.2 g (0.1 mole) of N-phenylpiperazine and 350 ml of 2-propanol was heated at reflux for 16 hr. The white crystalline precipitate which formed on standing at room temperature was filtered. The resulting white crystalline solid was identified as the hydrochloride salt of the N-phenylpiperazine. The filtrate was mixed with 60 ml of ethereal hydrogen chloride and precipitated in ether. The white crystalline solid was filtered off and recrystallized with acetone to give 17.6 g of title compound, m.p. 186°–188° C.

Analysis: Calculated for $C_{21}H_{29}Cl_3N_2O_2$: C, 56.32; H, 6.53;
N, 6.25;
Found: C, 56.07; H, 6.47;
N, 6.24.

EXAMPLE 3

1-(3,5-Dimethylphenoxy)-4-(4-phenyl-1-piperazinyl)-2-butanol

A mixture of 11.5 g (0.05 mole) of 1-(3,5-dimethyl-2-hydroxybutyl chloride and 16 g (0.1 mole) of N-phenylpiperazine was heated at 120°–140° C. for 15 min. The reaction mixture was heated with 500 ml acetone to boiling. The solid which precipitated was filtered off at room temperature. The solid was washed with cold water, then with acetone. One half of the crystalline solid was neutralized with dilute sodium hydroxide at 75°. Recrystallization from methanol-water mixture gave 5 g white crystalline solid, m.p. 88°–90° C.

Analysis: Calculated for $C_{22}H_{30}N_2O_2$: C, 74.54; H, 8.53;
N, 7.90;
Found: C, 74.36; H, 8.61;
N, 8.03.

EXAMPLE 4

1-Phenoxy-4-[4-(2-pyridinyl)-1-piperazinyl]-2-butanol dimaleate

A mixture which contained 15 g (0.75 mole) of 1-phenoxy-4-chloro-2-butanol and 16.3 g (0.1 mole) of N-(2-pyridyl)piperazine was heated at 120° C. for 0.5 hr. The resulting reaction mixture was heated with 300 ml of 3N hydrochloric acid. The acidic solution was extracted twice with isopropyl ether (150 ml each) at room temperature and made basic. The oily precipitate was extracted into isopropyl ether, concentrated to dryness and dried over sodium sulfate to give 18.6 g of the free base of the title compound.

Fifteen grams (0.46 mole) of the free base, 10.6 g (0.92 mole) of maleic acid and 300 ml isopropanol was heated to give a solution which was then cooled.

The resulting precipitate was filtered off and recrystallized from isopropanol to give 22.5 g of the maleate salt, m.p. 123°–125° C.

Analysis: Calculated for $C_{27}H_{33}N_3O_{10}$: C, 57.96; H, 5.94;
N, 7.51;
Found: C, 57.71; H, 5.82;
N, 7.30.

EXAMPLE 5

1-(2-Methoxyphenoxy)-4-[4-(2-pyridinyl)-1-piperazinyl]-2-butanol trihydrochloride monohydrate A mixture of 11.5 g (0.05 mole) of 1-(o-methoxyphenoxy)-2-hydroxybutyl chloride and 8 g (0.05 mole) of 2-pyridylpiperazine was heated at 100° C. for 15 min. The reaction mixture was extracted with 200 ml of 3N hydrochloric acid solution, washed with ether, then made basic with sodium hydroxide. The oily precipitate was extracted into isopropyl ether and the solution was dried over sodium sulfate and concentrated to dryness. The gummy residue was dissolved in a small amount of isopropanol and treated with ethereal hydrogen chloride and precipitated in anhydrous ether. The white crystalline precipitate was recrystallized with acetone twice to give 8 g of trihydrochloride monohydrate, m.p. 95°–97° C.

Analysis: Calculated for $C_{20}H_{35}Cl_3N_3O_4$: C, 49.24; H, 7.23;
N, 8.61;
Found: C, 49.18; H, 6.99; N, 8.85.

EXAMPLE 6

1-Phenoxy-4-(4-phenyl-1-piperazinyl)-2-butanol

A mixture of 6.5 g (0.04 mole) of 1-phenylpiperazine, 8.4 g (0.042 mole) of 4-chloro-1-phenoxy-2-butanol and 15.9 g (0.15 mole) of anhydrous sodium carbonate in 200 ml of 1-butanol was heated at reflux 20 hr. The mixture was concentrated under reduced pressure and the residue was partitioned between water and benzene. The benzene layer was washed with water and aqueous saturated sodium chloride solution, dried over sodium sulfate and concentrated under reduced pressure to give the title product in the residue which was recrystallized from isopropyl alcohol to give 8.9 g (68%) of white powder, m.p. 93°–94° C.

Analysis: Calculated for $C_{20}H_{26}N_2O_2$: C, 73.59; H, 8.03; N, 8.58;
Found: C, 73.48; H, 8.09; N, 8.56.

EXAMPLE 7

1-(4-Chlorophenoxy)-4-(4-phenyl-1-piperazinyl)-2-butanol

This compound was prepared according to the procedure of Example 6. A mixture of 3.2 g (0.02 mole) of 1-phenyl piperazine, 4.9 g (0.021 mole) of 4-chloro-1-(4-chlorophenoxy)-2-butanol and 8.0 g (0.075 mole) of anhydrous sodium carbonate in 100 ml of 1-butanol gave 3.8 g (53%) of white powder, m.p. 83°–85° C. Recrystallizing solvent used was isopropyl alcohol.

Analysis: Calculated for $C_{20}H_{25}ClN_2O_2$: C, 66.57; H, 6.98;
N, 7.76;
Found: C, 66.65; H, 7.08;
N, 7.69.

EXAMPLE 8

1-(2-Methoxyphenoxy)-4-(4-phenyl-1-piperazinyl)-2-butanol

This compound was prepared according to the procedure of Example 6. A mixture of 3.2 g (0.02 mole) of 1-phenylpiperazine, 4.8 g (0.02 mole) of 4-chloro-1-(2-methoxyphenoxy)-2-butanol and 8.0 g (0.075 mole) of anhydrous sodium carbonate in 100 ml of 1-butanol gave 4.5 g (64%) of white powder, m.p. 101°–102° C. Recrystallizing solvent used was isopropyl alcohol.

Analysis: Calculated for $C_{21}H_{28}N_2O_3$: C, 70.76; H, 7.92; N, 7.86;
Found: C, 70.47; H, 8.04; N, 7.76.

EXAMPLE 9

1-(4-Chloro-3-methylphenoxy)-4-(4-phenyl-1-piperazinyl)-2-butanol

This compound was prepared according to the procedure of Example 6. A mixture of 2.4 g (0.015 mole) of 1-phenylpiperazine, 3.7 g (0.015 mole) of 4-chloro-1-(4-chloro-3-methylphenoxy)-2-butanol and 5.3 g (0.05 mole) of anhydrous sodium carbonate in 100 ml of 1-butanol gave 3.6 g (64%) of white solid, 102°–103° C. Recrystallizing solvent used was isopropyl alcohol.

Analysis: Calculated for $C_{21}H_{27}ClN_2O_2$: C, 67.28; H, 7.26; N, 7.47;
Found: C, 67.42; H, 7.35; N, 7.37.

EXAMPLE 10

1-(4-Phenyl-phenoxy)-4-(4-phenyl-1-piperazinyl)-2-butanol

This compound was prepared according to the procedure of Example 6. A mixture of 2.4 g (0.015 mole) of 4-chloro-1-[4-(1,1'-biphenyl)yloxy]-2-butanol and 5.3 g (0.05 mole) of anhydrous sodium carbonate in 100 ml of 1-butanol gave 3.7 g (62%) of white solid, m.p. 101°–106° C. Recrystallizing solvent used was isopropyl alcohol.

Analysis: Calculated for $C_{26}H_{30}N_2O_2$: C, 77.58; H, 7.51; N, 6.96;
Found: C, 77.33; H, 7.55; N, 6.74.

EXAMPLE 11

1-Phenoxy-4-[4-(4-fluorophenyl)-1-piperazinyl]-2-butanol

This compound was prepared according to the procedure of Example 6. A mixture of 3.6 g (0.02 mole) of 1-(4-fluorophenyl)piperazine, 4.0 g (0.02 mole) of 4-chloro-1-phenoxy 2-butanol and 5.3 g (0.05 mole) of anhydrous sodium carbonate in 100 ml of 1-butanol gave 5.1 g (74%) of offwhite powder, m.p. 97°–99° C. Recrystallizing solvent used was isopropyl alcohol.

Analysis: Calculated for $C_{20}H_{25}FN_2O_2$: C, 69.75; H, 7.32; N, 8.13;
Found: C, 69.78; H, 7.34; N, 8.06.

EXAMPLE 12

1-(3-Trifluoromethylphenoxy)-4-(4-phenyl-1-piperazinyl)-2-butanol

This compound was prepared according to the procedure of Example 6. A mixture of 2.4 g (0.015 mole) of 1-phenylpiperazine, 4.0 g (0.015 mole) of 4-chloro-1-(3-trifluoromethylphenoxy)-2-butanol and 5.3 g (0.05 mole) of anhydrous sodium carbonate in 100 ml of 1-butanol gave 2.5 g (42%) of a tan powder, m.p. 73°–74° C. Recrystallizing solvent used was ligroin.

Analysis: Calculated for $C_{21}H_{25}F_3N_2O_2$: C, 63.95; H, 6.39; N, 7.10;
Found: C, 63.87; H, 6.41; N, 6.99.

EXAMPLE 13

1-Phenoxy-4-[4-(4-methoxyphenyl)-1-piperazinyl]-2-butanol

This compound was prepared according to the procedure of Example 6. A mixture of 4.8 g (0.025 mole) of 1-(4-methoxyphenyl)piperazine, 5.0 g (0.025 mole) of 4-chloro1-phenoxy-2-butanol and 8.0 g (0.075 mole) of anhydrous sodium carbonate in 100 ml of 1-butanol gave 6.4 g (72%) of tan towder., m.p. 95°–97° C. Recrystallizing solvent used was isopropyl alcohol.

Analysis: Calculated for $C_{21}H_{28}N_2O_3$: C, 70.76; H, 7.92; N, 7.86;
Found: C, 70.43; H, 7.89; N, 7.68.

EXAMPLE 14

1-Phenoxy-4-[4-(2-methoxyphenyl)-1-piperazinyl]-2-butanol

This compound was prepared according to the procedure of Example 6. A mixture of 2.9 g (0.015 mole) of 1-(2-methoxyphenyl)piperazine (95%), 3.0 g (0.015 mole) of 4-chloro-1-phenoxy-2-butanol and 5.3 g (0.05 mole) of anhydrous sodium carbonate in 100 ml of 1- butanol gave 4.0 g (75%) of off-white powder, m.p. 74°-76° C. Recrystallizing solvent used was isopropyl alcohol.

Analysis: Calculated for $C_{21}H_{28}N_2O_3$: C, 70.76; H, 7.92; N, 7.86;

Found: C, 70.72; H, 7.88; N, 7.78.

EXAMPLE 15

1-Phenoxy-4-[4-(4-chlorophenyl)-1-piperazinyl]-2-butanol

This compound was prepared according to the procedure of Example 6. A mixture of 3.0 g (0.015 mole) of 1-(p-chlorophenyl)piperazine, 3.0 g (0.015 mole) of 4-chloro-1-phenoxy-2-butanol and 5.3 g (0.05 mole) of anhydrous sodium carbonate in 100 ml of 1-butanol gave 3.8 g (70%) of off-white powder, m.p. 108°-110° C. Recrystallizing solvent used was isopropyl alcohol.

Analysis: Calculated for $C_{20}H_{25}ClN_2O_2$: C, 66.57; H, 6.98; N, 7.76;

Found: C, 66.60; H, 7.10; N, 7.72.

EXAMPLE 16

1-Phenoxy-4-[4-(3-methoxyphenyl)-1-piperazinyl]-2-butanol

This compound was prepared according to the procedure of Example 6. A mixture of 3.8 g (0.02 mole) of 1-(3-methoxyphenyl)piperazine, 4.0 g (0.02 mole) of 4-chloro-1phenoxy-2-butanol and 8.0 g (0.075 mole) of anhydrous sodium carbonate in 150 ml of 1-butanol gave 3.3 g (45%) of off-white powder, m.p. 58°-60° C. Recrystallizing solvent used was diethyl ether-petroleum ether.

Analysis: Calculated for $C_{21}H_{28}N_2O_3$: C, 70.76; H, 7.92; N, 7.86;

Found: C, 70.66; H, 8.00; N, 7.82.

EXAMPLE 17

1-Phenoxy-4-[4-(3-trifluoromethylphenyl)-1-piperazinyl]2-butanol

This compound was prepared according to the procedure of Example 6. A mixture of 3.5 g (0.015 mole) of N-(α, α, αtrifluoro-m-tolyl)piperazine, 3.0 g (0.015 mole) of 4-chloro1-phenoxy-2-butanol and 5.3 g (0.05 mole) of anhydrous sodium carbonate in 100 ml of 1-butanol gave 3.9 g (66%) of white powder, m.p. 83°-84° C. The recrystallizing solvent used in isopropyl alcohol.

Analysis: Calculated for $C_{21}H_{25}F_3N_2O_2$: C, 63.95; H, 6.39; N, 7.10;

Found: C, 64.10; H, 6.46; N, 7.09.

EXAMPLE 18

1-Phenoxy-4-[4-(3-chlorophenyl)-1-piperazinyl]-2-butanol

The compound was prepared according to the procedure of Example 6. A mixture of 3.0 g (0.015 mole) of 1-(3-chlorophenyl)piperazine, 3.0 g (0.015 mole) of 4-chloro-1-phenoxy-2-butanol, 5.3 g (0.05 mole) of anhydrous sodium carbonate and 100 ml of 1-butanol gave 3.7 g (69%) of white powder, m.p. 76°-78° C. The recrystallizing solvent used was isopropyl alcohol.

Analysis: Calculated for $C_{20}H_{25}ClN_2O_2$: C, 66.57; H, 6.98; N, 7.76;

Found: C, 66.47; H, 6.97; N, 7.72.

EXAMPLE 19

1-Phenoxy-4-[4-(2-chlorophenyl)-1-piperazinyl]-2-butanol

This compound was prepared according to the procedure of Example 6. A mixture of 3.0 g (0.015 mole) of 1-(2-chlorophenyl)piperazine, 3.0 g (0.015 mole) of 4-chloro-1-phenoxy-2-butanol, 5.3 g (0.05 mole) of anhydrous sodium carbonate and 100 ml of 1-butanol gave an oil as residue. The oil was purified by chromatography on 75 g of silica gel to yield 1.3 g (24%) of white powder, m.p. 53°-55° C. The recrystallizing solvent was diethyl ether.

Analysis: Calculated for $C_{20}H_{25}ClN_2O_2$: C, 66.57; H, 6.98; N, 7.76;

Found: C, 66.96; H, 7.03; N, 7.69.

EXAMPLE 20

1-(4-Chlorophenoxy)-4-[4-(4-fluorophenyl)-1-piperazinyl]-2-butanol

This compound was prepared according to the procedure of Example 6. A mixture of 1.8 g (0.01 mole) of 1-(4-fluorophenyl)-piperazine, 2.4 g (0.01 mole) of 4-chloro-1-(4-chlorophenoxy)-2-butanol and 5.3 g (0.05 mole) of anhydrous sodium carbonate in 100 ml of 1-butanol gave 1.4 g (37%) of white powder, m.p. 90°-92° C. The recrystallizing solvent used was isopropyl ether.

Analysis: Calculated for $C_{20}H_{24}ClFN_2O_2$: C, 63.40; H, 6.39; N, 7.39;

Found: C, 63.76; H, 6.49; N, 7.31.

EXAMPLE 21

1-Phenoxy-4-[4-(3,4-dichlorophenyl)-1-piperazinyl]-2-butanol

This compound was prepared according to the procedure of Example 6. A mixture of 2.3 g (0.01 mole) of 1-(3,4-dichlorophenyl)piperazine, 2.0 g (0.01 mole) of 4-chloro-1-phenoxy-2-butanol and 5.3 g (0.05 mole) of anhydrous sodium carbonate in 100 ml of 1-butanol gave 2.5 g (63%) of off-white powder, m.p. 120.5°-121.5° C. The recrystallizing solvent was isopropyl alcohol.

Analysis: Calculated for $C_{20}H_{24}Cl_2N_2O_2$: C, 60.76; H, 6.12; N, 7.09;

Found: C, 60.71; H, 6.19; N, 7.07.

EXAMPLE 22

1-Phenoxy-4-[4-(4-methylphenyl)-1-piperazinyl]-2-butanol

This compound was prepared according to the procedure of Example 6. A mixture of 1.8 g (0.01 mole) of 1-(4-methylphenyl)piperazine, 2.2 g (0.01 mole) of 4-chloro-1-phenoxy-2-butanol and 5.3 g (0.05 mole) of anhydrous sodium carbonate in 100 ml of 1-butanol gave 2.1 g (62%) of off-white powder, m.p. 90°-92° C. The recrystallizing solvent used was isopropyl alcohol.

Analysis: Calculated for $C_{21}H_{28}N_2O_2$: C, 74.08; H, 8.29; N, 8.23;

Found: C, 74.43; H, 8.38; N, 8.22.

EXAMPLE 23

1-Phenoxy-4-[4-(4-bromophenyl)-1-piperazinyl]-2-butanol

This compound was prepared according to the procedure of Example 6. A mixture of 2.4 g (0.01 mole) of the base of 1-(4-bromophenyl)-piperazine, 2.0 g (0.01 mole)

of 4-chloro-1-phenoxy-2-butanol, 5.3 g (0.05 mole) of anhydrous sodium carbonate and 0.3 g of potassium iodide in 100 ml of 1-butanol gave 3.0 g (73%) of white powder, m.p. 125°–126° C. The recrystallizing solvent used was isopropyl alcohol.

Analysis: Calculated for $C_{20}H_{25}BrN_2O_2$: C, 59.27; H, 6.22; N, 6.91;

Found: C, 58.96; H, 6.22; N, 7.03.

EXAMPLE 24

1-Phenoxy-4-[4-(4-acetylphenyl)-1-piperazinyl]-2-butanol

This compound was prepared according to the procedure of Example 6. A mixture of 2.0 g (0.01 mole) of 4-(1-piperazino) acetophenone, 2.0 g (0.01 mole) of 4-chloro-1-phenoxy-2-butanol, 5.3 g (0.05 mole) of anhydrous sodium carbonate and 0.3 g of potassium iodide in 100 ml of 1-butanol gave 3.0 g (81%) of pale yellow solid, m.p. 113.5°–117° C. The recrystallizing solvent was isopropyl alcohol.

Analysis: Calculated for $C_{22}H_{28}N_2O_3$: C, 71.71; H, 7.66; N, 7.60;

Found: C, 71.95; H, 7.70; N, 7.55.

EXAMPLE 25

1-(4-Bromophenoxy)-4-(4-phenyl-1-piperazinyl)-2-butanol

A mixture of 8.4 g (0.03 mole) of 1-(4-bromophenoxy)-4-chloro-2-butanol, 4.9 g (0.03 mole) of 1-phenylpiperazine, 16.0 g (0.15 mole) of sodium carbonate, and 0.3 g (0.002 mole) of potassium iodide in a total volume of 200 ml of 1 butanol was heated at reflux with stirring for 16 hr. The suspended solids were collected by filtration and the hot filtrate was concentrated under reduced pressure to give a golden oil as residue. The oil was partitioned between cold 10% sodium hydroxide solution and benzene. The benzene layer was washed three times with 50 ml portions of water, dried with anhydrous magnesium sulfate and concentrated under reduced pressure to give an oil that crystallized when triturated with petroleum ether (30°–60° b.p. range). The solid was recrystallized from ethyl ether and then from ethanol-benzene to give 4.3 g (35%) of white solid, m.p. 100°–103° C.

Analysis: Calculated for $C_{20}H_{25}BrN_2O_2$: C, 59.26; H, 6.22; N, 6.91;

Found: C, 59.25; H, 6.29; N, 6.91.

EXAMPLE 26

1-(4-Methylphenoxy)-4-(4-phenyl-1-piperazinyl)-2-butanol

This compound was prepared according to the procedure of Example 25. A mixture of 6.5 g (0.03 mole) of 4-chloro-1-(4-methylphenoxy)-2-butanol, 4.9 g (0.03 mole) of 1-phenylpiperazine, 16.0 g (0.15 mole) of anhydrous sodium carbonate, and 0.3 g (0.002 mole) of potassium iodide in a total volume of 200 ml of 1-butanol gave 6.4 g (63%) of white solid, m.p. 123°–125° C. The recrystallizing solvent used was a mixture of benzene and petroleum ether.

Analysis: Calculated for $C_{21}H_{28}N_2O_2$: C, 74.08; H, 8.29; N, 8.23;

Found: C, 73.91; H, 8.32; N, 8.18.

EXAMPLE 27

1-(4-Fluorophenoxy)-4-(4-phenyl-1-piperazinyl)-2-butanol

This compound was prepared according to the procedure of Example 25. A mixture of 6.6 g (0.03 mole) of 4-chloro-1-(4-fluorophenoxy)-2-butanol, 4.9 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave 5.5 g (53%) of white solid, m.p. 71°–73° C. The recrystallizing solvent used was a mixture of benzene and petroleum ether.

Analysis: Calculated for $C_{20}H_{25}FN_2O_2$: C, 69.74; H, 7.32; N, 8.13;

Found: C, 69.70; H, 7.33; N, 8.09.

EXAMPLE 28

1-(4-Cyanophenoxy)-4-(4-phenyl-1-piperazinyl)-2-butanol dihydrochloride

This compound was prepared according to the procedure of Example 25. A mixture of 6.8 g (0.03 mole) of 4-chloro-1-(4-cyanophenoxy)-2-butanol, 4.9 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave an oil as residue. The hydrochloric acid salt was formed in ethereal hydrogen chloride and the collected solid was recrystallized from methanolethyl ether to give 3.7 g (35%) of white solid, m.p. 195°–198° C.

Analysis: Calculated for $C_{21}H_{27}Cl_2N_3O_2$: C, 59.44; H, 6.41; N, 9.90;

Found: C, 59.69; H, 6.48; N, 9.89.

EXAMPLE 29

1-(4-Methoxyphenoxy)-4-(4-phenyl-1-piperazinyl)-2-butanol

This compound was prepared according to the procedure of Example 25. A mixture of 6.9 g (0.03 mole) of 4-chloro-1-(4-methoxyphenoxy)-2-butanol, 4.9 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave an oil which solidified. The collected solid was recrystallized from 2-propanol to give 2.9 g (27%) of white crystalline powder, m.p. 103°–105° C.

Analysis: Calculated for $C_{21}H_{28}N_2O_2$: C,70.76; H,7.92; N,7.86;

Found: C,70.66; H,7.94; N,7.81.

EXAMPLE 30

1-(3,4-Dichlorophenoxy)-4-(4-phenyl-1-piperazinyl)-2-butanol dihydrochloride

This compound was prepared according to the procedure of Example 25. A mixture of 8.1 g (0.03 mole) of 4-chloro-1-(3,4-dichlorophenoxy)-2-butanol, 4.9 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave a golden oil as residue. The hydrochloric acid salt was formed in ethereal hydrogen chloride and the collected solid was recrysrallized from methanol-ethyl ether to give 5.1 g (37%) of white solid, m.p. 210°–213° C.

Analysis: Calculated for $C_{20}H_{26}Cl_4N_2O_2$: C,51.30; H,5.60;

N,5.98;
Found: C,51.53; H,5.63; N,6.01.

EXAMPLE 31

1-(4-Nitrophenoxy)-4-(4-phenyl-1-piperazinyl)-2-butanol dihydrochloride

This compound was prepared according to the procedure of Example 25. A mixture of 12.3 g (0.05 mole) of 4-chloro-1-(4-nitrophenoxy)-2-butanol, 8.1 g (0.05 mole) of 1-phenylpiperazine, and 26.0 g (0.25 mole) of anhydrous sodium carbonate in a total volume of 250 ml of 1-butanol gave a golden oil as residue. The hydrochloride was formed in ethereal hydrogen chloride and the collected solid was recrystallized thrice from methanol-water to give 1.1 g (5%) of white solid, m.p. 195°–200° C.

Analysis: Calculated for $C_{20}H_{27}Cl_2N_3O_4$: C,54.06; H,6.13; N,9.46;
Found: C,54.03; H,6.14; N,9.48.

EXAMPLE 32

1-(4-Chlorophenoxy)-4-[4-(2-pyridyl)-1-piperazinyl]-2-butanol dihydrochloride

This compound was prepared according to the procedure of Example 25. A mixture of 5.0 g (0.03 mole) of 1-(2-pyridyl)piperazine, 7.0 g (0.03 mole) of 4-chloro-1-(4-chlorophenoxy)-2-butanol, 16.0 g (0.15 mole) of anhydrous sodium carbonate and 0.3 g (0.002 mole) of potassium iodide in a total volume of 200 ml of 1-butanol gave a golden oil as residue. The hydrochloride was formed in 2-propanol saturated with hydrogen chloride and the collected solid was recrystallized from aqueous 2-propanol to give 8.1 g (62%) of white solid, m.p. >245° C.

Analysis: Calculated for $C_{19}H_{26}Cl_3N_3O_2$: C,52.49; H,6.03; N,9.66;
Found: C,52.43; H,6.09; N,9.70.

EXAMPLE 33

1-(4-Aminocarbonylphenoxy)-4-(4-phenylpiperazino)-2-butanol monohydrochloride

This compound was prepared according to the procedure of Example 25. A mixture of 7.3 g (0.03 mole) of 4-(4-chloro-2-hydroxybutoxy)benzamide, 5.0 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave a cream colored semi-solid as residue. The hydrochloric acid salt was formed in 2-propanol saturated with hydrogen chloride, and the collected solid was recrystallized from methanol-water to give 4.8 g (40%) of white solid, m.p. 238°–241° C.

Analysis: Calculated for $C_{21}H_{28}ClN_3O_3$: C,62.14; H,6.95; N,10.35;
Found: C,62.11; H,6.96; N,10.36.

EXAMPLE 34

1-(4-Tertiarybutylphenoxy)-4-(4-phenyl-1-piperazinyl)-2-butanol monohydrochloride This compound was prepared according to the procedure of Example 25. A mixture of 7.7 g (0.03 mole) of 4-chloro-1-[4-(1,1-dimethylethyl)phenoxy]-2-butanol, 5.0 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave a golden oil as residue. The hydrochloric acid salt was formed in 2-propanol saturated with hydrogen chloride, and the collected solid was recrystallized from 2-propanolmethanol-water to give 6.0 g (48%) of white, crystalline solid, m.p. 190°–193° C.

Analysis: Calculated for $C_{24}H_{35}ClN_2O_2$: C,68.80; H,8.42; N,6.69;
Found: C,68.78; H,8.45; N,6.68.

EXAMPLE 35

1-(4-Fluorophenoxy)-4-[4-(4-fluorophenyl)-1-piperazinyl]-2-butanol monohydrochloride This compound was prepared according to the procedure of Example 25. A mixture of 6.5 g (0.03 mole) of 4-chloro-1-(4-fluorophenoxy)-2-butanol, 5.4 g (0.03 mole) of 1-(4-fluorophenyl)piperazine, 16.0 g (0.15 mole) of anhydrous sodium carbonate and 0.3 g (0.002 mole) of potassium iodide in a total volume of 200 ml of 1-butanol gave a golden oil as residue. The hydrochloric acid salt was formed in 2-propanol saturated with hydrogen chloride, and the collected solid was recrystallized from methanol-water-ethyl ether to give 6.7 g (56%) of white solid, m.p. 161°–165° C.

Analysis: Calculated for $C_{20}H_{25}ClF_2N_2O_2$: C,60.22; H,6.32; N,7.02;
Found: C,59.87; H,6.29; N,6.97.

EXAMPLE 36

1-(4-Acetylphenoxy)-4-(4-phenyl-1-piperazinyl)-2-butanol dihydrochloride

This compound was prepared according to the procedure of Example 25. A mixture of 7.3 g (0.03 mole) of 1-[4-(4-chloro-2-hydroxybutoxy)phenyl]ethanone, 5.0 g (0.03 mole) of 1-phenylpiperazine, 16.0 g (0.15 mole) of anhydrous sodium carbonate and 0.3 g (0.002 mole) of potassium iodide in a total volume of 200 ml of 1-butanol gave a brown oil as residue. The hydrochloric acid salt was formed in 2-propanol saturated with hydrogen chloride, and the collected solid was recrystallized from 95% ethanol to give 5.6 g (42%) of pale yellow solid, m.p. 203°–208° C.

Analysis: Calculated for $C_{22}H_{30}Cl_2N_2O_3$: C,59.87; H,6.85; N,6.35;
Found: C,59.86; H,7.01; N,6.32.

EXAMPLE 37

1-(4-Fluorophenoxy)-4-[4-(2-pyridinyl)-1-piperazinyl]-2-butanol dihydrochloride

This compound was prepared according to the procedure of Example 25. A mixture of 6.6 g (0.03 mole) of 4-chloro-1-(4-fluorophenoxy)-2-butanol, 4.9 g (0.03 mole) of 1-(2-pyridyl)piperazine, 16.0 g (0.15 mole) of anhydrous sodium carbonate and 0.3 g of potassium iodide in a total volume of 200 ml of 1-butanol gave a golden oil as residue. The hydrochloride was formed in 2-propanol saturated with hydrogen chloride and the collected solid was recrystallized from methanol/water to give 9.0 g (72%) of white solid, m.p. >245° C.

Analysis: Calculated for $C_{19}H_{26}Cl_2FN_3O_2$: C,54.55; H,6.27; N,10.04;

Found: C,54.57; H,6.34; N,10.16.

EXAMPLE 38

1-(4-Fluorophenoxy)-4-[4-(2-pyridinyl)-1-piperazinyl]-2-butanol

A mixture of 9.0 g (0.0413 mole) of 4-chloro-(4-fluorophenoxy)-2-butanol, 6.8 g (0.0414 mole) of 1-(2-pyridinyl)piperazine, 14.5 g (0.1374 mole) of anhydrous sodium carbonate and 0.24 g of potassium iodide in 200 ml of 1-butanol was heated at reflux for 20 hr. The mixture was concentrated under reduced pressure and the residue was partitioned between 200 ml of water and 200 ml of benzene. The benzene layer was washed with water and brine, dried over sodium sulfate and concentrated under reduced pressure to give a thick yellow oil. Upon trituration with petroleum ether (30°–60° C.), the oil solidified. The collected solid was recrystallized from ligroin to yield 8.2 g (57%) of white, crystalline solid, m.p. 72°–73° C.

Analysis: Calculated for $C_{19}H_{24}FN_3O_2$: C,66.07; H,7.00; N,12.17;
Found: C,66.05; H,7.11; N,12.31.

EXAMPLE 39

1-(4-Fluorophenoxy)-4-[4-(4-methylphenyl)-1-piperazinyl]-2-butanol dihydrochloride This compound was prepared according to the procedure of Example 25. A mixture of 1.8 g (0.01 mole) of 1-(4-methylphenyl)piperazine, 2.2 g (0.01 mole) of 4-chloro-1-(4-fluorophenoxy)-2-butanol, 5.2 g (0.05 mole) of anhydrous sodium carbonate, and 0.1 g of potassium iodide in a total volume of 200 ml of 1-butanol gave a golden oil as residue. The hydrochloride was formed in 2-propanol saturated with hydrogen chloride and the collected solid was recrystallized from methanol-water-ethyl ether to give 1.8 g (41%) of white solid, m.p. 200°–205° C.

Analysis: Calculated for $C_{21}H_{29}Cl_2FN_2O_2$: C,58.47; H,6.78; N,6.49;
Found: C,58.67; H,6.82; N,6.54.

EXAMPLE 40

1-(4-Chloro-3-methylphenoxy)-4-[4-(4-fluorophenyl)-1-piperazinyl]-2-butanol

This compound was prepared according to the procedure of Example 25. A mixture of 1.8 g (0.01 mole) of 1-(4-fluorophenyl)piperazine, 2.5 g (0.01 mole) of 4-chloro-1-(4-chloro-3-methylphenoxy)-2-butanol, 5.2 g (0.05 mole) of anhydrous sodium carbonate and 0.1 g of potassium iodide in a total volume of 200 ml of 1-butanol gave a golden oil as residue. The hydrochloride was formed in 2-propanol saturated with hydrogen chloride and the collected solid was recrystallized from methanol-water-ethyl ether to give 1.7 g (36%) of white solid, m.p. 199°–203° C.

Analysis: Calculated for $C_{21}H_{28}Cl_3FN_2O_2$: C,54.15; H,6.06; N,6.01;
Found: C,54.48; H,6.20; N,6.07.

EXAMPLE 41

1-(4-Chlorophenoxy)-4-[4-(4-chlorophenyl)-1-piperazinyl]-2-butanol dihydrochloride This compound was prepared according to the procedure of Example 25. A mixture of 3.2 g (0.016 mole) of 1-(4-chlorophenyl)piperazine, 3.8 g (0.016 mole) of 4-chloro-1-(4-chlorophenoxy)-2-butanol, 8.3 g (0.078 mole) of anhydrous sodium carbonate and 0.1 g of potassium iodide in a total volume of 200 ml of 1-butanol gave a golden oil as residue. The hydrochloride was formed in 2-propanol saturated with hydrogen chloride and the collected solid was recrystallized from methanol-water-ethyl ether to give 3.6 g (47%) of white solid, m.p. 195°–200° C.

Analysis: Calculated for $C_{20}H_{26}Cl_4N_2O_2$: C,51.30; H,5.60; N,5.98;
Found: C,51.57; H,5.70; N,6.07.

EXAMPLE 42

1-(4-Fluorophenoxy)-4-[4-(4-chlorophenyl)-1-piperazinyl]-2-butanol monohydrochloride monohydrate This compound was prepared according to the procedure of Example 25. A mixture of 3.2 g (0.016 mole) of 1-(4-chlorophenyl)piperazine, 3.6 g (0.016 mole) of 4-chloro-1-(4-fluorophenoxy)-2-butanol, 8.3 g (0.078 mole) of anhydrous sodium carbonate and 0.1 g of potassium iodide in a total volume of 200 ml of 1-butanol gave a golden oil as residue. The hydrochloride was formed in 2-propanol saturated with hydrogen chloride and the collected solid was recrystallized from methanol-water-ethyl ether to give 2.9 g (40%) of white solid, m.p. 183°–186° C.

Analysis: Calculated for $C_{20}H_{27}Cl_2FN_2O_3$: C,55.43; H,6.28; N,6.46;
Found: C,55.13; H,5.99; N,6.49.

EXAMPLE 43

1-(4-Chlorophenoxy)-4-[4-(4-methylphenyl)-1-piperazinyl]-2-butanol monohydrochloride sesquihydrate This compound was prepared according to the procedure of Example 25. A mixture of 1.8 g (0.01 mole) of 1-(4-methylphenyl)piperazine, 2.4 g (0.01 mole) of 4-chloro-1-(4-chlorophenoxy)-2-butanol, 5.2 g (0.05 mole) of anhydrous sodium carbonate and 0.1 g of potassium iodide in a total volume of 200 ml of 1-butanol gave a golden oil as residue. The hydrochloride was formed in 2-propanol saturated with hydrogen chloride and the collected solid was recrystallized from ethanol-water-ethyl ether to give 1.4 g (31%) of white solid, m.p. 190°–195° C.

Analysis: Calculated for $C_{21}H_{28}Cl_2N_2O_2.1.5H_2O$: C,57.54; H,7.13; N,6.39;
Found: C,57.67; H,6.71; N,6.40.

EXAMPLE 44

1-(4-Chloro-3-methylphenoxy)-4-[4-(2-pyridyl)-1-piperazinyl]-2-butanol dihydrochloride This compound was prepared according to the procedure of Example 25. A mixture of 1.6 g (0.01 mole) of 1-(2-pyridyl)piperazine, 2.5 g (0.01 mole) of 4-chloro-1-(4-chloro-3-methylphenoxy)-2-butanol, 5.2 g (0.05 mole) of anhydrous sodium carbonate and 0.1 g of potassium iodide in a total volume of 200 ml of 1-butanol gave a golden oil as residue. The hydrochloride was formed in 2-propanol saturated with hydrogen chloride and the collected solid was recrystallized from methanol-water-ethyl ether to give 2.9 g (65%) of white solid, m.p. >250° C.

Analysis: Calculated for $C_{20}H_{28}Cl_3N_3O_2$: C,53.53; H,6.29;
N,9.36;
Found: C,53.50; H,6.33;
N,9.38.

EXAMPLE 45

1-(4-Chlorophenoxy)-4-[4-(4-methoxyphenyl)-1-piperazinyl]-2-butanol dihydrochloride This compound was prepared according to the procedure of Example 25. A mixture of 3.0 g (0.015 mole) of 1-(4-methoxyphenyl)-piperazine, 3.7 g (0.015 mole) of 4-chloro-1-(4-chlorophenoxy)-2-butanol, 5.2 g (0.05 mole) of anhydrous sodium carbonate and 0.1 g of potassium iodide in a total volume of 200 ml of 1-butanol gave an oil as residue. The hydrochloride was formed in 2-propanol saturated with hydrogen chloride and the collected solid was recrystallized from methanol-water to give 3.3 g (42%) of white, crystalline solid, m.p. 220°-225° C.

Analysis: Calculated for $C_{21}H_{29}Cl_3N_2O_3$: C,54.38; H,6.30;
N,6.04;
Found: C,54.37; H,6.31;
N,6.07.

EXAMPLE 46

1-(4-Fluorophenoxy)-4-[4-(4-methoxyphenyl)-1-piperazinyl]-2-butanol monohydrochloride monohydrate This compound was prepared according to the procedure of Example 25. A mixture of 3.0 g (0.015 mole) of 1-(4-methoxyphenyl)piperazine, 3.4 g (0.015 mole) of 4-chloro-1-(4-fluorophenoxy)-2-butanol, 5.2 g (0.05 mole) of anhydrous sodium carbonate and 0.1 g of potassium iodide in a total volume of 200 ml of 1-butanol gave an oil as residue. The hydrochloride was formed in 2-propanol saturated with hydrogen chloride and the collected solid was recrystallized from methanol-water-ethyl ether to give 3.2 g (48%) of white solid, m.p. 195°-202° C.

Analysis: Calculated for $C_{21}H_{28}ClFN_2O_3.H_2O$: C,58.81; H,7.05;
N,6.53;
Found: C,58.98; H,6.81;
N,6.48.

EXAMPLE 47

1-(4-Fluorophenoxy)-4-[4-(4-methoxyphenyl)-1-piperazinyl]-2-butanol

This compound was prepared according to the procedure of Example 25. A mixture of 5.8 g (0.0267 mole) of 4-chloro-1-(4-fluorophenoxy)-2-butanol, 5.1 g (0.0267 mole) of 1-(4-methoxyphenyl)piperazine, 9.4 g (0.089 mole) of anhydrous sodium carbonate, and 0.16 g of potassium iodide in a total volume of 200 ml of 1-butanol gave a brown oil. Upon trituration with petroleum ether (30°-60° C.), the oil solidified. The collected solid was recrystallized from isopropyl ether to yield 6.4 g (64%) of white, crystalline solid, m.p. 78°-80° C.

Analysis: Calculated for $C_{21}H_{27}FN_2O_3$: C,67.36; H,7.27;
N,7.48;
Found: C,67.35; H,7.36;
N,7.53.

EXAMPLE 48

1-(3,5-Dimethylphenoxy)-4-[4-(4-fluorophenyl)-1-piperazinyl]-2-butanol monohydrochloride monohydrate This compound was prepared according to the procedure of Example 25. A mixture of 2.5 g (0.01 mole) of 4-chloro-1-(3,5-dimethylphenoxy)-2-butanol, 1.8 g (0.01 mole) of 1-(4-fluorophenyl)piperazine, 5.2 g (0.05 mole) of anhydrous sodium carbonate and 0.1 g of potassium iodide in a total volume of 200 ml of 1-butanol gave a golden oil as residue. The hydrochloride was formed in 2-propanol saturated with hydrogen chloride and the collected solid was recrystallized from methanol-water-ethyl ether to give 1.6 g (37%) of white crystalline solid, m.p. 176°-180° C.

Analysis: Calculated for $C_{22}H_{30}ClFN_2O_2.H_2O$: C,61.89; H,7.56;
N,6.56;
Found: C,61.84; H,7.28;
N,6.54.

EXAMPLE 49

1-(4-Fluorophenoxy)-4-[4-(4-acetylphenyl)-1-piperazinyl]-2-butanol

This compound was prepared according to the procedure of Example 6. A mixture of 2.0 g (0.01 mole) of 4-(1-piperazino)acetophenone, 2.2 g (0.01 mole) of 4-chloro-1-(4-fluorophenoxy)-2-butanol, 5.3 g (0.05 mole) of anhydrous sodium carbonate and 0.3 g of potassium iodide in 100 ml of 1-butanol gave 2.7 g (69%) of pale yellow solid, m.p. 114°-116° C. The recrystallizing solvent used was isopropyl alcohol.

Analysis: Calculated for $C_{22}H_{27}FN_2O_3$: C,68.37; H,7.04; N,7.25;
Found: C,68.37; H,7.15; N,7.28.

EXAMPLE 50

1-(4-Chlorophenoxy)-4-[4-(4-acetylphenyl)-1-piperazinyl]2-butanol

This compound was prepared according to the procedure of Example 6. A mixture of 2.0 g (0.01 mole) of 4-(1-piperazino)acetophenone, 2.4 g (0.01 mole) of 4-chloro-1-(4-chlorophenoxy)-2-butanol, 5.3 g (0.05 mole) of anhydrous sodium carbonate and 0.3 g of potassium iodide in 100 ml of 1-butanol gave 2.8 g (70%) of pale yellow solid, m.p. 123°-125° C. The recrystallizing solvent was isopropyl alcohol.

Analysis: Calculated for $C_{22}H_{27}ClN_2O_3$: C,65.58; H,6.75;
N,6.95;
Found: C,65.60; H,6.82;
N,6.95.

EXAMPLE 51

1-Phenoxy-4-[4-(3,4,5-trimethoxyphenyl)-1-piperazinyl]-2-butanol oxalate [2:3]

This compound was prepared according to the procedure of Example 6. A mixture of 2.5 g (0.01 mole) of 1-(3,4,5-trimethoxyphenyl)piperazine, 2.0 g (0.01 mole) of 1-phenoxy-4-chloro-2-butanol and 2.5 g (0.01 mole) of anhydrous sodium carbonate in 100 ml of 1-butanol gave a red-brown gum as residue. The gum was converted to the oxalic acid salt and the salt was recrystallized from absolute ethanol to give 3.2 g (58%) of tan powder, m.p. 154°–156° C.

Analysis: Calculated for $C_{26}H_{35}N_2O_{11}$: C,56.62; H,6.40; N,5.08;
Found: C,56.60; H,6.52; N,5.23.

EXAMPLE 52

1-Phenoxy-4-[4-(4-cyanophenyl)-1-piperazinyl]-2-butanol

Following the procedure of Example 25, the title compound is prepared from 4-chloro-1-phenoxy-2-butanol and 4-(1-piperazinyl)benzonitrile.

EXAMPLE 53

1-Phenoxy-4-[4-(4-aminocarbonyl)-1-piperazinyl]-2-butanol

Following the procedure of Example 25, the title compound is prepared from 4-chloro-1-phenoxy-2-butanol and 4-(1-piperazinyl)benzamide.

EXAMPLE 54

1-Phenoxy-4-[4-(4-nitrophenyl)-1-piperazinyl]-2-butanol

Following the procedure of Example 25, the title compound is prepared from 4-chloro-1-phenoxy-2-butanol and 1-(4-nitrophenyl)piperazine.

EXAMPLE 55

1-Phenoxy-4-[4-(4-aminophenyl)-1-piperazinyl]-2-butanol

The title compound is prepared by catalytic reduction of 1-phenoxy-4-[4-(4-nitrophenyl)-1-piperazinyl]-2-butanol with hydrogen over palladium on carbon.

EXAMPLE 56

1-Phenoxy-4-[4-(4-acetylaminophenyl)-1-piperazinyl]-2-butanol

Following the procedure of Example 25, the title compound is prepared from 4-chloro-1-phenoxy-2-butanol and N-[4-(1-piperazinyl)phenyl]acetamide.

EXAMPLE 57

1-Phenoxy-4-[4-(4-ethoxycarbonylphenyl)-1-piperazinyl]-2-butanol

Following the procedure of Example 25, the title compound is prepared from 4-(1-piperazinyl)benzoic acid ethyl ester and 4-chloro-1-phenoxy-2-butanol.

EXAMPLE 58

1-Phenoxy-4-[4-(4-carboxyphenyl)-1-piperazinyl]-2-butanol sodium salt

The title compound is prepared in aqueous solution by hydrolysis of 1-phenoxy-4-[4-(4-ethoxycarbonylphenyl)-1-piperazinyl]-2-butanol in aqueous sodium carbonate solution. The free carboxylic acid derivative may be obtained by neutralizing with an acid such as hydrochloric acid.

EXAMPLE 59 *a* to *d*

When in the procedure of Example 51 the following are substituted for 1-phenoxy-4-chloro-2-butanol:
1-(4-chloro-3,5-dimethylphenoxy)-4-chloro-2-butanol,
1-(2-chloro-4,5-dimethylphenoxy)-4-chloro-2-butanol,
1-(4-bromo-2,6-dimethylphenoxy)-4-chloro-2-butanol, and,
1-(2,4-dichloro-6-nitrophenoxy)-4-chloro-2-butanol,
there are obtained:
(a) 1-(4-chloro-3,5-dimethylphenoxy)-4-[4-(3,4,5-trimethoxyphenyl)-1-piperazinyl]-2-butanol oxalate,
(b) 1-(2-chloro-4,5-dimethylphenoxy)-4-[4-(3,4,5-trimethoxyphenyl)-1-piperazinyl]-2-butanol oxalate,
(c) 1-(4-bromo-2,6-dimethylphenoxy)-4-[4-(3,4,5-trimethoxyphenyl)-1-piperazinyl]-2-butanol oxalate, and
(d) 1-(2,4-dichloro-6-nitrophenoxy)-4-[4-(3,4,5-trimethoxyphenyl)-1-piperazinyl]-2-butanol oxalate.

EXAMPLE 60 *a* and *b*

When in the procedure of Example 44 the following are substituted for 1-(2-pyridyl)piperazine:
1-(3-pyridyl)piperazine, and
1-(4-pyridyl)piperazine, there are obtained:
(a) 1-(4-chloro-3-methylphenoxy)-4-[4-(3-pyridyl)-1-piperazinyl]-2-butanol dihydrochloride, and
(b) 1-(4-chloro-3-methylphenoxy)-4-[4-(4-pyridyl)-1-piperazinyl]-2-butanol dihydrochloride.

EXAMPLE 61 *a* and *b*

Following the procedure of Example 25, 1-(4-chlorophenyl)piperazine is reacted with each of the following:
4-chloro-1-(4-acetylaminophenoxy)-2-butanol, and,
4-chloro-1-(4-ethoxycarbonylphenoxy)-2-butanol, to give,
(a) 1-(4-acetylaminophenoxy)-4-[4-(4-chlorophenyl)-1-piperazinyl]-2-butanol hydrochloride, and
(b) 1-(4-ethoxycarbonylphenoxy)-4-[4-(4-chlorophenyl)-1-piperazinyl]-2-butanol hydrochloride.

EXAMPLE 62

1-(4-Carboxy)phenoxy-4-[4-(4-chlorophenyl)-1-piperazinyl]-2-butanol sodium salt

The title compound is prepared in aqueous solution by hydrolysis of 1-(4-ethoxycarbonylphenoxy)-4-[4-(4-chlorophenyl)-1-piperazinyl]-2-butanol in aqueous sodium carbonate solution. The free carboxylic acid derivative may be obtained by neutralizing with an acid such as hydrochloric acid.

EXAMPLE 63

1-(3-Trifluoromethylphenoxy)-4-[4-(2-pyridinyl)-1-piperazinyl]-2-butanol

This compound was prepared according to the procedure used to synthesize the compound of Example 6. A mixture of 3.3 g (0.02 mole) of 1-(2-pyridyl)piperazine, 5.4 g (0.02 mole) of 4-chloro-1-(3-trifluoromethylphenoxy)-2-butanol, 6.4 g (0.06 mole) of anhydrous sodium carbonate and 0.4 g of potassium iodide in 100 ml of 1-butanol gave 2.8 g (35%) of the title compound as an off-white solid, m.p. 81°–81.5° C. Recrystallizing solvent used was isopropyl ether.

Analysis: Calculated for $C_{20}H_{24}F_3N_3O_2$: C,60.75; H,6.12; N,10.63;
Found: C,60.57; H,6.13; N,10.59.

TABLE 1

Structures of Compounds in the Examples

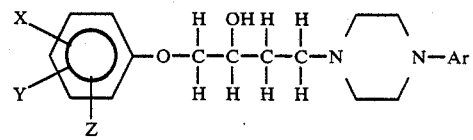

| Ex. No. | X | Y | Z | Ar | Salt |
|---|---|---|---|---|---|
| 1 | 2-Cl | H | H | $C_6H_5-$ | — |
| 2 | 2-CH$_3$ | 4-Cl | H | $C_6H_5-$ | 2HCl |
| 3 | 3-CH$_3$ | 5-CH$_3$ | H | $C_6H_5-$ | — |
| 4 | H | H | H | 2-pyridinyl | 2 maleate |
| 5 | 2-OCH$_3$ | H | H | 2-pyridinyl | 3 HCl.H$_2$O |
| 6 | H | H | H | $C_6H_5-$ | — |
| 7 | 4-Cl | H | H | $C_6H_5-$ | — |
| 8 | 2-OCH$_3$ | H | H | $C_6H_5-$ | — |
| 9 | 3-CH$_3$ | 4-Cl | H | $C_6H_5-$ | — |
| 10 | 4-C$_6$H$_5$— | — | — | $C_6H_5-$ | — |
| 11 | H | H | H | 4-F—C$_6$H$_4$— | — |
| 12 | 3-CF$_3$ | H | H | $C_6H_5-$ | — |
| 13 | H | H | H | 4-OCH$_3$—C$_6$H$_4$— | — |
| 14 | H | H | H | 2-OCH$_3$—C$_6$H$_4$— | — |
| 15 | H | H | H | 4-Cl—C$_6$H$_4$— | — |
| 16 | H | H | H | 3-OCH$_3$—C$_6$H$_4$— | — |
| 17 | H | H | H | 3-CF$_3$—C$_6$H$_4$— | — |
| 18 | H | H | H | 3-Cl—C$_6$H$_4$— | — |
| 19 | H | H | H | 2-Cl—C$_6$H$_4$— | — |
| 20 | 4-Cl | H | H | 4-F—C$_6$H$_4$— | — |
| 21 | H | H | H | 3,4-(Cl$_2$)$_2$—C$_6$H$_3$— | — |
| 22 | H | H | H | 4-CH$_3$—C$_6$H$_4$— | — |
| 23 | H | H | H | 4-Br—C$_6$H$_4$— | — |
| 24 | H | H | H | 4-[C(O)CH$_3$]—C$_6$H$_4$— | — |
| 25 | 4-Br | H | H | $C_6H_5-$ | — |
| 26 | 4-CH$_3$ | H | H | $C_6H_5-$ | — |
| 27 | 4F | H | H | $C_6H_5-$ | — |
| 28 | 4-CN | H | H | $C_6H_5-$ | 2 HCl |
| 29 | 4-OCH$_3$ | H | H | $C_6H_5-$ | — |
| 30 | 3-Cl | 4-Cl | H | $C_6H_5-$ | 2 HCl |
| 31 | 4-NO$_2$ | H | H | $C_6H_5-$ | — |
| 32 | 4-Cl | H | H | 2-pyridinyl | 2 HCl |
| 33 | 4-C(O)NH$_2$ | H | H | $C_6H_5-$ | HCl |
| 34 | 2-C(CH$_3$)$_3$ | H | H | $C_6H_5-$ | HCl |
| 35 | 4-F | H | H | 4-F—C$_6$H$_5$— | HCl |
| 36 | 4-C(O)CH$_3$ | H | H | $C_6H_5-$ | 2 HCl |
| 37 | 4-F | H | H | 2-pyridinyl | 2 HCl |
| 38 | 4-F | H | H | 2-pyridinyl | — |
| 39 | 4-F | H | H | 4-CH$_3$—C$_6$H$_4$— | 2 HCl |
| 40 | 3-CH$_3$ | 4-Cl | H | 4-F—C$_6$H$_4$— | — |
| 41 | 4-Cl | H | H | 4-Cl—C$_6$H$_4$— | 2 HCl |
| 42 | 4-F | H | H | 4-Cl—C$_6$H$_4$— | HCl.H$_2$O |
| 43 | 4-Cl | H | H | 4-CH$_3$—C$_6$H$_4$— | HCl.1.5 H$_2$O |
| 44 | 3-CH$_3$ | 4-Cl | H | 2-pyridinyl | 2 HCl |
| 45 | 4-Cl | H | H | 4-OCH$_3$—C$_6$H$_4$— | 2 HCl |
| 46 | 4-F | H | H | 4-OCH$_3$—C$_6$H$_4$— | HCl.H$_2$O |
| 47 | 4-F | H | H | 4-OCH$_3$C$_6$H$_4$— | — |
| 48 | 3-CH$_3$ | 5-CH$_3$ | H | 4-F—C$_6$H$_4$— | HCl.H$_2$O |
| 49 | 4-F | H | H | 4-C(O)CH$_3$—C$_6$H$_4$— | — |
| 50 | 4-Cl | — | H | 4-[C(O)CH$_3$]—C$_6$H$_4$— | — |
| 51 | H | H | H | 3,4,5-(OCH$_3$)—C$_6$H$_4$— | oxalate [2:3] |
| 52 | H | H | H | 4-CN—C$_6$H$_4$— | — |
| 53 | H | H | H | 4-[C(O)NH$_2$]—C$_6$H$_4$— | — |
| 54 | H | H | H | 4-NO$_2$—C$_6$H$_4$— | — |
| 55 | H | H | H | 4-NH$_2$—C$_6$H$_4$— | — |
| 56 | H | H | H | 4-[NHC(O)CH$_3$]—C$_6$H$_4$— | — |
| 57 | H | H | H | 4-[C(O)OC$_2$H$_5$]—C$_6$H$_4$— | — |
| 58 | H | H | H | 4-(COO$^-$)—C$_6$H$_4$— | Na |
| 59 (a) | 4-Cl | 3-CH$_3$ | 5-CH$_3$ | 3,4,5-(OCH$_3$)$_3$—C$_6$H$_2$— | oxalate |
| (b) | 2-Cl | 4-CH$_3$ | 5-CH$_3$ | 3,4,5-(OCH$_3$)$_3$—C$_6$H$_2$ | oxalate |

TABLE 1-continued
Structures of Compounds in the Examples

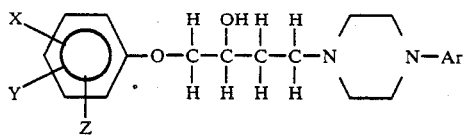

| Ex. No. | X | Y | Z | Ar | Salt |
|---|---|---|---|---|---|
| (c) | 4-Br | 2-CH$_3$ | 6-CH$_3$ | 3,4,5-(OCH$_3$)$_3$—C$_6$H$_2$— | oxalate |
| (d) | 2-Cl | 4-Cl | 6-NO$_2$ | 3,4,5-(OCH$_3$)$_3$—C$_6$H$_2$— | oxalate |
| 60 (a) | 4-Cl | 3-CH$_3$ | H | 3-pyridinyl | 2 HCl |
| (b) | 4-Cl | 3-CH$_3$ | H | 4-pyridinyl | 2 HCl |
| 61 (a) | 4-NHC(O)CH$_3$ | H | H | 4-Cl—C$_6$H$_4$— | HCl |
| | 4-[C(O)OC$_2$H$_5$]— | H | H | 4-Cl—C$_6$H$_4$— | HCl |
| 62 | 4-COO$^-$ | H | H | 4-Cl—C$_6$H$_4$— | Na |
| 63 | 3-CF$_3$— | H | H | 2-pyridinyl | — |

PHARMACOLOGY METHODS

Antiallergy Screening Method—Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205–209 (1977) which measures the effect of oral administration of the compound on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 255). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml) ± S.D. A significant decrease (p<0.05) in the edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency.

Guinea Pig Anaphylaxis Method

The method used to test antiallergy effectiveness of the compounds in guinea pigs as compared to other drugs is as follows:

Guinea pigs are first sensitized to egg albumin (EA, Sigma Chemical Co., St. Louis, Mo.), at least 20 days prior to aerosol challenge by receiving 0.5 ml of EA-Al(OH)$_3$ conjugate (33 µg EA/ml) intramuscularly in each hind leg.

On the test day, fasted, sensitized guinea pigs are divided into a control group (8 animals per group) and test groups of four animals per group by using random number tables generated by an IBM scrambler. The reference; e.g., theophylline or test drug (Formula I cpd.) dissolved or suspended in 0.5% Tween 80 in distilled water or the control article (0.5% Tween 80 in distilled water) are administered orally in a volume of liquid at 10 ml/kg. Either 1, 5, or 24 hours following the oral administration of the test drug, reference drug, or control article, each animal is placed in an aerosolization chamber. EA (10 mg/ml) aerosolized at a rate of 10 liters of air/min is delivered into the chamber for a maximum of 5 minutes. The anaphylactic response consists of coughing, dyspnea, reeling, collapse and death. Upon collapsing, the animals are removed from the chamber. Animals are considered protected if they do not collapse within 5 min of exposure to the aerosolized antigen. The number of animals that collapse in each group is recorded. ED$_{50}$ for collapse is calculated by the method of Litchfield and Wilcoxon (1949), J. PHARMACOL. EXP. THERAP. 95, 99–113 for evaluation of dose-effect experiments. Comparisons of ED$_{50}$s from different experimental trials and determinations of relative potency are determined by the Litchfield and Wilcoxon method, ibid. The following conditions must be met before an experiment is acceptable:

(1) Control group shows collapse in ⅞ or 8/8 animals, and
(2) Theophylline reference group shows protection in ¾ or 4/4 animals treated 1 hr or 5 hr prior to antigen exposure.

Pharmaceutical Compositions and Administration

Compositions for administration to living animals are comprised of at least one of the compounds of Formula I according to the antiallergy method of the invention in association with a pharmaceutical carrier or excipient. Effective quantitites of the compounds may be administered in any one of various ways, for example, orally as in elixirs, capsules, tablets or coated tablets, parenterally in the form of sterile solutions, suspensions, and in some cases intravenously in the form of sterile solutions, intranasally and to the throat or bronchial region in the form of drops, gargles, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or arachis oil contained in ampuls.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the pharmacology tests on guinea pigs in comparison to certain other antiallergy drugs suggest an effective dose for an adult will be in the range of 1.0 to 20 mg for the more active compounds with a daily dosage amounting to about 4 to 160 mg/day.

Based on the animal data, unit dosages containing an amount of compound equivalent to about 0.02 to 0.2 mg of active drug per kilogram of body weight are contemplated. Daily dosages of about 0.10 to 2.0 mg/kg of body weight are contemplated for humans and obviously several small dosage forms may be administered at one time. However, the amount of the active compounds administered need not be limited by these contemplations due to uncertainty in transposing animal data to human treatment.

Examples of compositions within the preferred ranges given are as follows:

| Capsules | | |
|---|---|---|
| | Ingredients | Per Cap. |
| 1. | Active ingredient | 10.00 mg |
| 2. | Lactose | 146.000 mg |
| 3. | Magnesium Stearate | 4.000 mg |

Procedure
1. Blend 1, 2 and 3.
2. Mill this blend and blend again.
3. This milled blend is then filled into #1 hard gelatin capsules.

| Tablets | | |
|---|---|---|
| | Ingredients | Mg./Tab. |
| 1. | Active ingredient | 10.0 mg |
| 2. | Corn Starch | 20.0 mg |
| 3. | Alginic acid | 20.0 mg |
| 4. | Sodium alginate | 20.0 mg |
| 5. | Magnesium Stearate | 1.3 mg |

Procedure
1. Blend 1, 2, 3 and 4.
2. Add sufficient water portionwise to the blend from step #1 with careful stirring after each addition. Such additions of water and stirring continue until the mass is of consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | | |
|---|---|---|
| | Ingredients | Per ml. |
| 1. | Active ingredient | 1.0 mg |
| 2 | pH 4.0 Buffer solution | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | | |
|---|---|---|
| | Ingredients | Per ml |
| 1. | Active ingredient | 5.0 mg |
| 2 | Isotonic Buffer solution 4.0 | q.s to 1.0 ml |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | | |
|---|---|---|
| | Ingredients | Per Supp. |
| 1. | Active ingredient | 10.0 mg |
| 2. | Polyethylene Glycol 1000 | 1350.0 mg |
| 3. | Polyethylene Glycol 4000 | 450.0 mg |

Procedure
1. Melt 2 and 3 together and stir until uniform.
2. Dissolve #1 in the molten mass from step 1 and stir until uniform.
3. Pour the molten mass from step 2 into suppoository molds and chill.
4. Remove the suppositories from molds and wrap.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:
1. A method of combatting Type I allergic response in a living animal body in need thereof which comprises administering to said animal an effective amount of a compound selected from the group having the formula:

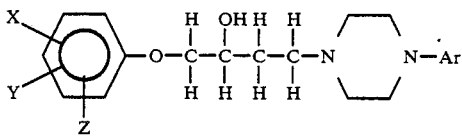

wherein Ar is selected from

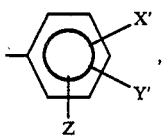

or 2,3 or 4-pyridyl;
X and X' are selected from
hydrogen,
loweralkyl,
loweralkoxy,
halogen,
trifluoromethyl,
nitro,
amino,
acetylamino,
pheny, or

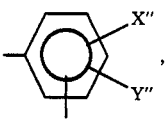

acetyl,
cyano,
aminocarbonyl,
carboxy, or
loweralkyl carboxylic acid ester;
Y,Y',Y" and X" are selected from the same group as X and X' except phenyl and substituted phenyl are excluded;
Z and Z' are selected from
hydrogen,
loweralkyl, or
loweralkoxy,
and the pharmaceutically acceptable salts and hydrates thereof.

2. The method of claim 1 wherein the compound used is 1-(2-chlorophenoxy)-4-(4-phenyl-1-piperazinyl)-2-butanol or a pharmaceutically acceptable salt thereof.

3. The method of claim 1 wherein the compound used is 1-(4-chloro-2-methylphenoxy)-4-(4-phenyl-1-piperazinyl or a pharmaceutically acceptable salt thereof.

4. The method of claim 1 wherein the compound used is 1-(3,5-dimethylphenoxy)-4-(4-phenyl-1-piperazinyl)-2-butanol or a pharmaceutically acceptable salt thereof.

5. The method of claim 1 wherein the compound used is 1-phenoxy-4-[4-(2-pyridinyl)-1-piperazinyl]-2-butanol or a pharmaceutically acceptable salt thereof.

6. The method of calim 1 wherein the compound used is 1-(2-methoxyphenoxy)-4-[4-(2-pyridinyl)-1-piperazinyl]-2-butanol or a pharmaceutically acceptable salt thereof.

7. The method of claim 1 wherein the compound used is 1-phenoxy-4-(4-phenyl-1-piperazinyl)-2-butanol or a pharmaceutically acceptable salt thereof.

8. The method of claim 1 wherein the compound used is 1-(4-chlorophenoxy)-4-(4-phenyl-1-piperazinyl)-2-butanol or a pharmaceutically acceptable salt thereof.

9. The method of claim 1 wherein the compound used is 1-(2-methoxyphenoxy)-4-(4-phenyl-1-piperazinyl)-2-butanol or a pharmaceutically acceptable salt thereof.

10. The method of claim 1 wherein the compound used is 1-(4-chloro-3-methylphenoxy)-4-(4-phenyl-1-piperazinyl)-2butanol or a pharmaceutically acceptable salt thereof.

11. The method of claim 1 wherein the compound used is 1-(4-phenylphenoxy)-4-(4-phenyl-1-piperazinyl)-2-butanol or a pharmaceutically acceptable salt thereof.

12. The method of claim 1 wherein the compound used is 1-phenoxy-4-[4-(4-fluorophenyl)-1-piperazinyl]-2-butanol or a pharmaceutically acceptable salt thereof.

13. The method of claim 1 wherein the compound used is 1-(3-trifluoromethylphenoxy)-4-(4-phenyl-1-piperazinyl)-2-butanol or a pharmaceutically acceptable salt thereof.

14. The method of claim 1 wherein the compound used is 1-phenoxy-4-[4-(4-methoxyphenyl)-1-piperazinyl]-2-butanol or a pharmaceutically acceptable salt thereof.

15. The method of claim 1 wherein the compound used is 1-phenoxy-4-[4-(2-methoxyphenyl)-1-piperazinyl]-2-butanol or a pharmaceutically acceptable salt thereof.

16. The method of claim 1 wherein the compound used is 1-phenoxy-4-[4-(4-chlorophenyl)-1-piperazinyl]-2-butanol or a pharmaceutically acceptable salt thereof.

17. The method of claim 1 wherein the compound used is 1-phenoxy-4-[4-(3-methoxyphenyl)-1-piperazinyl]-2-butanol or a pharmaceutically acceptable salt thereof.

18. The method of claim 1 wherein the compound used is 1-phenoxy-4-[4-(3-trifluoromethylphenyl)-1-piperazinyl]-2-butanol or a pharmaceutically acceptable salt thereof.

19. The method of claim 1 wherein the compound used is 1-phenoxy-4-[4-(3-chlorophenyl)-1-piperazinyl]-2-butanol or a pharmaceutically acceptable salt thereof.

20. The method of claim 1 wherein the compound used is 1-phenoxy-4-[4-(2-chlorophenyl)-1-piperazinyl]-2-butanol or a pharmaceutically acceptable salt thereof.

21. The method of claim 1 wherein the compound used is 1-(4-chlorophenoxy)-4-[4-(4-fluorophenyl)-1-piperazinyl]-2-butanol or a pharmaceutically acceptable salt thereof.

22. The method of claim 1 wherein the compound used is 1-phenoxy-4-[4-(3,4-dichlorophenyl)-1-piperazinyl]-2-butanol or a pharmaceutically acceptable salt thereof.

23. The method of claim 1 wherein the compound used is 1-phenoxy-4-[4-(4-methylphenyl)-1-piperazinyl-2-butanol or a pharmaceutically acceptable salt thereof.

24. The method of claim 1 wherein the compound used is 1-phenoxy-4-[4-(4-bromophenyl)-1-piperazinyl]-2-butanol or a pharmaceutically acceptable salt thereof.

25. The method of claim 1 wherein the compound used is 1-phenoxy-4-[4-(4-acetylphenyl)-1-piperazinyl]-2-butanol or a pharmaceutically acceptable salt thereof.

26. The method of claim 1 wherein the compound used is 1-(4-bromophenoxy)-4-(4-phenyl-1-piperazinyl)-2-butanol or a pharmaceutically acceptable salt thereof.

27. The method of claim 1 wherein the compound used is 1-(4-methylphenoxy)-4-(4-phenyl-1-piperazinyl)-2-butanol or a pharmaceutically acceptable salt thereof.

28. The method of claim 1 wherein the compound used is 1-(4-fluorophenoxy)-4-(4-phenyl-1-piperazinyl)-2-butanol or a pharmaceutically acceptable salt thereof.

29. The method of claim 1 wherein the compound used is 1-(4-cyanophenoxy)-4-(4-phenyl-1or a pharmaceutically acceptable salt thereof.

30. The method of claim 1 wherein the compound used is 1-(4-methoxyphenoxy)-4-(4-phenyl-1or a pharmaceutically acceptable salt thereof.

31. The method of claim 1 wherein the compound used is 1-(3-4-dichlorophenoxy)-4-(4-phenyl-1-piperazinyl)-2-butanol or a pharmaceutically acceptable salt thereof.

32. The method of claim 1 wherein the compound used is 1-(4-nitrophenoxy)-4-(4-phenyl-1-piperazinyl)-2-butanol or a pharmaceutically acceptable salt thereof.

33. The method of claim 1 wherein the compound used is 1-(4-chlorophenoxy)-4-[4-(2-pyridinyl)-1-piperazinyl]-2-butanol or a pharmaceutically acceptable salt thereof.

34. The method of claim 1 wherein the compound used is 1-(4-aminocarbonylphenoxy)-4-(4-phenyl-piperazino)-2-butanol or a pharmaceutically acceptable salt thereof.

35. The method of claim 1 wherein the compound used is 1-(4-tertiarybutylphenoxy)-4-(4-phenyl-1-piperazinyl)-2-butanol or a pharmaceutically acceptable salt thereof.

36. The method of claim 1 wherein the compound used is 1-(4-fluorophenoxy)-4-[4-(4-fluorophenyl)-1-piperazinyl]-2-butanol or a pharmaceutically acceptable salt thereof.

37. The method of claim 1 wherein the compound used is 1-(4-acetylphenoxy)-4-(4-phenyl-1-piperazinyl)-2-butanol or a pharmaceutically acceptable salt thereof.

38. The method of claim 1 wherein the compound used is 1-(4-fluorophenoxy)-4-[4-(2-pyridinyl)-1-piperazinyl]-2-butanol or a pharmaceutically acceptable salt thereof.1

39. The method of claim 1 wherein the compound used is 1-(4-fluorophenoxy)-4-[4-(4-methylphenyl)-1-piperazinyl]-2-butanol or a pharmaceutically acceptable salt thereof.

40. The method of claim 1 wherein the compound used is 1-(4-chloro-3-methylphenoxy)-4-[4-(4-fluorophenyl)-1-piperazinyl-2-butanol or a pharmaceutically acceptable salt thereof.

41. The method of claim 1 wherein the compound used is 1-(4-chlorophenoxy)-4-[4-(4-chlorophenyl)-1-piperazinyl]-2-butanol or a pharmaceutially acceptable salt thereof.

42. The method of claim 1 wherein the compound used is 1-(4-fluorophenoxy)-4-[4-(4-chlorophenyl)-1-piperazinyl-2-butanol or a pharmaceutically acceptable salt thereof.

43. The method of claim 1 wherein the compound used is 1-(4-chlorophenoxy)-4-[4-(4-methylphenyl)-1-piperazinyl]-2-butanol or a pharmaceutically acceptable salt thereof.

44. The method of claim 1 wherein the compound used is 1-(4-chloro-3-methyolphenoxy)-4-[4-(2-pyridinyl)-1piperazinyl]-2-butanol or a pharmaceutically acceptable salt thereof.

45. The method of claim 1 wherein the compound used is 1-(4-chlorophenoxy)-4-[4-(4-methoxyphenyl)-1-piperazinyl]-2-butanol or a pharmaceutically acceptable salt thereof.

46. The method of claim 1 wherein the compound used is 1-(4-fluorophenoxy)-4-[4-(4-methosyphenyl)-1-piperaiznyl]-2-butanol or a pharmaceutically acceptable salt thereof.

47. The method of claim 1 wherein the compound used is 1-(3,5-dimethylphenoxy)-4-[4-(4-fluorophenyl)-1-piperazinyl]-2-butanol or a pharmaceutically acceptable salt thereof.

48. the method of claim 1 wherein the compound used is 1-(4-fluorophenoxy)-4-[4-(4-acetylphenyl)-1-piperazinyl]-2-butanol or a pharmaceutically acceptable salt thereof.

49. The method of claim 1 wherein the compound used is 1-(4-chlorophenoxy)-4-[4-(4-acetylphenyl)-1-piperazinly]-2-butanol or a pharmaceutically acceptable salt thereof.

50. The method of claim 1 wherein the compound used is 1-phenoxy-4-[4-(3,4,5-trimethoxyphenyl)-1-piperazinyl]-2-butanol or a pharmaceutially acceptable salt thereof.

51. The method of claim 1 wherein the compound used is 1-(3-trifluoromethylphenoxy)-4-[4-(2-pyridinyl)-1-piperazinyl]-2-butanol or a pharmaceutically acceptable salt thereof.

* * * * *